United States Patent [19]

Mohan et al.

[11] Patent Number: 5,731,311
[45] Date of Patent: Mar. 24, 1998

[54] N,N-DI(ARYL) CYCLIC UREA DERIVATIVES AS ANTI-COAGULANTS

[75] Inventors: Raju Mohan, Moraga; Michael M. Morrissey, Danville, both of Calif.

[73] Assignee: Berlex Laboratories, Inc., Richmond, Calif.

[21] Appl. No.: 764,374

[22] Filed: Dec. 12, 1996

Related U.S. Application Data

[62] Division of Ser. No. 458,598, Jun. 2, 1995, Pat. No. 5,612,363.

[51] Int. Cl.$^6$ ............... A61K 31/535; A61K 31/495; C07D 413/10; C07D 403/10
[52] U.S. Cl. ............ 514/235.8; 514/235.5; 514/252; 514/255; 514/318; 514/326; 514/333; 514/341; 514/392; 544/124; 544/139; 544/360; 544/370; 546/194; 546/210; 546/256; 546/274.1; 548/313.7; 548/314.4; 548/314.7; 548/316.4; 548/317.5; 548/318.5; 548/319.5; 548/320.1
[58] Field of Search ............... 544/124, 139, 544/360, 370; 546/194, 210, 256, 374.1; 548/313.7, 314.4, 314.7, 316.4, 317.5, 318.5, 319.5, 320.1; 514/235.5, 255, 235.8, 252, 318, 326, 338, 341, 392

[56] References Cited

U.S. PATENT DOCUMENTS

| | | |
|---|---|---|
| 5,276,049 | 1/1994 | Himmelsbach et al. |
| 5,332,822 | 7/1994 | Misra. |
| 5,478,942 | 12/1995 | Himmelsbach et al. |

FOREIGN PATENT DOCUMENTS

| | | |
|---|---|---|
| 0503548A1 | 3/1992 | European Pat. Off. |
| 0540051A1 | 10/1992 | European Pat. Off. |
| 0567966A1 | 4/1993 | European Pat. Off. |
| 0601459A2 | 12/1993 | European Pat. Off. |
| WO93/15756 | 8/1993 | WIPO. |
| WO94/13693 | 6/1994 | WIPO. |
| WO94/17817 | 8/1994 | WIPO. |

OTHER PUBLICATIONS

Tidwell, R. et al., "Strategies for Anticoagulation with Synthetic Protease Inhibitors, Xa Inhibitors Versus Thrombin Inhibitors," *Thrombosis Research*, (1980) 19:339–349.
Wagner, G. et al., "Synthese von a–a'–Bis[amidinobenzyliden]–und a–a' Bis–[amidinobenzyl]–cycloalkanonen," *Pharmazie*, (1977) 32,141–145.
Stürzebecher, J. et al., "Cyclic Amides of Nα–arysulfonylaminoacylated 4–amidinophenylalanine—Tight Binding Inhibitors of Thrombin," *Thrombosis Research*, (1983) 29:635–642.
Kikumoto, R. et al., "Selective inhibition of Thrombin by (2R,4R)–4–Methyl–1–[N²–[(3–methyl–1,2,3, 4–tetrahydro–8–quinolinyl)–sulfonyl]–L–arginyl)]–2piperidinecarboxylic Acid," *Biochemistry*, (1984) 23:85–90.

Stürzebecher, J. et al., "Synthetic Inhibitors of Serine Proteinases XXIII, Inhibition of Factor Xa by Diamidines", *Thrombosis Research*, (1980) 17:545:548.
Wagner, G. et al., "Synthese von N–Amidinobenzylverbindungen von Salicylamid, 2–4–Dioxodihydro–5,6–benzoxazin–(1.3) und–benzothiazin–(1.3) sowie von 2,4–Dioxo–1,2,3,4–tetrahydrochinazolin", *Die Pharmazie*, (1978) 33:15–19.

*Primary Examiner*—Patricia L. Morris
*Attorney, Agent, or Firm*—Carol J. Roth

[57] ABSTRACT

N,N-di(aryl) cyclic urea derivatives, such as the compounds of the following formula:

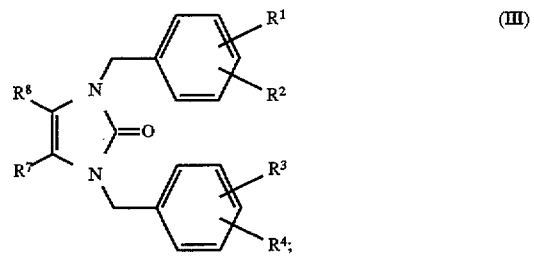

(III)

wherein $R^1$ is —C(NH)NH$_2$, —C(NH)N(H)OR$^{11}$, —C(NH)N(H)C(O)R$^9$, or —C(NH)N(H)C(O)OR$^{11}$;

$R^2$ and $R^3$ are independently hydrogen, halo, lower alkyl, lower haloalkyl, aryl, —OR$^{11}$, —C(O)OR$^{11}$, —C(O)N(R$^{11}$)R$^{12}$, —N(R$^{11}$)R$^{12}$, —N(H)C(O)R$^{11}$, or —N(H)S(O)$_2$R$^{11}$;

$R^4$ is halo, lower haloalkyl, imidazolyl, —C(NH)NH$_2$, —C(NH)NHOR$^{11}$, —C(NH)N(H)C(O)R$^5$, —C(NH)N(H)C(O)OR$^{11}$, —OR$^{11}$, —C(O)R$^{13}$, —(CH$_2$)$_n$C(O)OR$^{11}$ (where n is 0 to 6), —C(O)N(R$^{11}$)R$^{12}$, or —N(R$^{11}$)R$^{12}$;

$R^7$ and $R^8$ are independently hydrogen, lower alkyl, lower haloalkyl, 4-pyridinyl, —C(O)OR$^{11}$, —C(O)N(R$^{11}$)R$^{12}$, or aryl (optionally substituted by one or more substituents selected from the group consisting of halo, hydroxy, lower alkyl, lower haloalkyl, lower alkoxy and —N(R$^{11}$)R$^{12}$);

$R^{11}$ and $R^{12}$ are independently hydrogen, lower alkyl, aryl or lower aralkyl; or $R^{13}$ is pyrrolidinyl, 4-morpholinyl, piperazinyl, N-methylpiperazinyl, or piperidinyl; or a pharmaceutically acceptable salt thereof, are disclosed herein as being inhibitors of factor Xa and thereby being useful as anticoagulants.

2 Claims, No Drawings

N,N-DI(ARYL) CYCLIC UREA DERIVATIVES AS ANTI-COAGULANTS

This is a Division of appliction Ser. No. 08/458,598, filed Jun. 2, 1995, now U.S. Pat. No. 5,612,363.

FIELD OF THE INVENTION

The present invention is directed to N,N-di(aryl) cyclic urea derivatives and their phaceutically acceptable salts, which inhibit the enzymes in the coagulation cascade, such as fator Xa and factor IIa (thrombin), thereby being useful as anti-coagulants. It also relates to pharmaceutical composition containing the derivatives or their pharmaceutically acceptable salts, and their methods of use.

BACKGROUND OF THE INVENTION

Factor Xa is a member of trypsin-like serine protease class of enzymes. A one-to-one binding of factors Xa and Va with calcim ions and phospholipid forms the prothrombinase complex which converts prothrombin to factor IIa (thrombin). Thrombin, in turn, converts fibrinogen to fibrin which polymerizes to form insoluble fibrin.

In the coagulation cascade, the prothrombinase complex is the convergent point of the intrinsic (surface activated) and extrinsic (vessel injury-tissue factor) pathways (*Biochemistry* (1991), Vol. 30, p. 10363; and *Cell* (1988), Vol. 53, pp. 505–518). The model of the coagulation cascade has been refined further with the discovery of the mode of action of tissue factor pathway inhibitor (TFPI) (*Seminars in Hematology* (1992), Vol. 29, pp. 159–161). TFPI is a circulating multi-domain serine protease inhibitor with three kunitz-like domains which competes with factor Va for free factor Xa. Once formed, the binary complex of factor Xa and TFPI becomes a potent inhibitor of the factor VIIa and tissue factor complex.

Factor Xa can be activated by two distinct complexes, by tissue factor-factor VIIa complex on the "Xa burst" pathway and by the factor IXa-VIIA complex (TENase) of the "sustained Xa" pathway in the coagulation cascade. After vessel injury, the "Xa burst" pathway is activated via tissue factor (TF). Up relation of the coagulation cascade occurs via increased factor Xa production via the "sustained Xa" pathway. Down regulation of the coagulation cascade occurs with the formation of the factor Xa-TFPI complex, which not only removes factor Xa but also inhibits further factor formation via the "Xa burst" pathway. Consequently, there is a natural regulation of the coagulation cascade by factor Xa.

Published data with the proteins antistasin and tick anti-coagulant peptide (TAP) demonstrate that factor Xa inhibitors are efficacious anti-coagulants (*Thrombosis and Haemostasis* (1992), Vol. 67, pp. 371–376; and *Science* (1990), Vol. 248, pp. 593–596).

The active site of factor Xa can be blocked by either a mechanism-based or a tight binding inhibitor (a tight binding inhibitor differs from a mechanism-based inhibitor by the lack of a covalent link between the enzyme and the inhibitor). Two types of mechanism-based inhibitors are known, reversible and irreversible, which are distinguished by ease of hydrolysis of the enzyme-inhibitor link (*Thrombosis Res* (1992), Vol. 67, pp. 221–231; and *Trends Pharmacol. Sci.* (1987), Vol. 8, pp. 303–307). A series of guanidino compounds are examples of tight-binding inhibitors (*Thrombosis Res.* (1980), Vol. 19, pp. 339–349). Arylsulfonyl-arginine-piperidinecarboxylic acid derivatives have also been shown to be tight-binnding inhibitors of thrombin (*Biochem.* (1984), Vol. 23, pp. 85–90), as well as a series of arylamidine-containing compounds, including 3-amidinophenylaryl derivatives (*Thrombosis Res.* (1983), Vol. 29, pp. 635–642) and bis(amidino)benzyl cycloketones (*Thrombosis Res.* (1980), Vol. 17, pp. 545–548). Therapeutic utility of these compounds, however, is limited by their poor selectivity for factor Xa.

Related Disclosures

European Published Patent Application 0 540 051 (Nagahara et al.) describes aromatic amidine derivatives which are stated to be capable of showing a strong anticoagulant effect through reversible inhibition of factor Xa.

The synthesis of α,α'-bis(amidinobenzylidene) cycloalkanones and α,α'-bis(amidino-benzyl) cycloalkanones is described in *Pharmazie* (1977), Vol. 32, No. 3, pp. 141–145. These compounds are disclosed as being serine protease inhibitors.

SUMMARY OF THE INVENTION

This invention is directed to compounds or their pharmaceutically acceptable salts which are anti-coagulants by inhibiting enzymes in the coagulation cascade, such as human factor Xa and factor IIa (thrombin), and are therefore useful as pharmacological agents for the treatment of disease-states characterized by thrombotic activity.

Accordingly, in one aspect, this invention provides compounds selected from the group consisting of the following formulae:

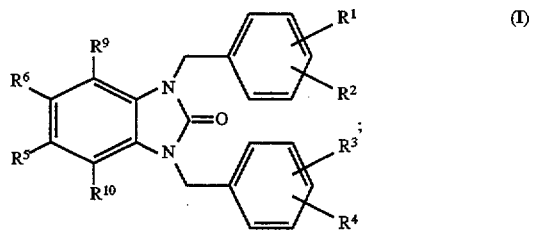

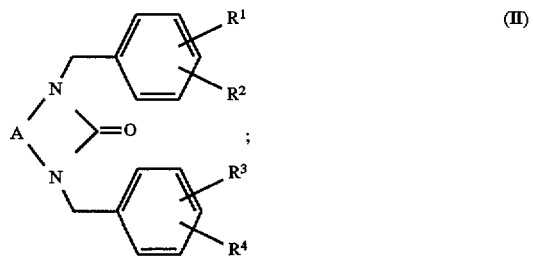

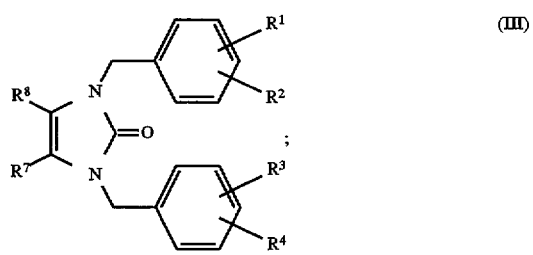

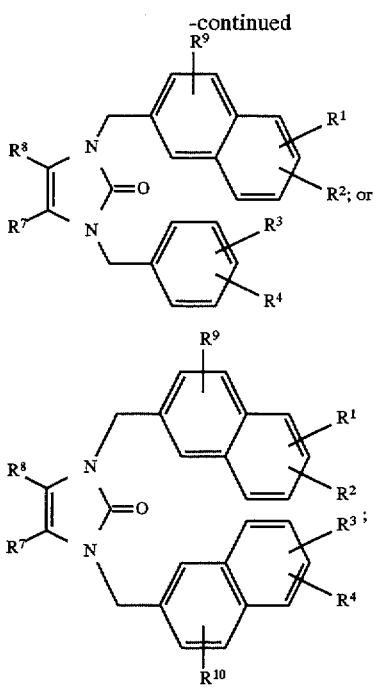

wherein

A is —C(R$^5$)R$^6$—(CH$_2$)$_m$—C(R$^9$)(R$^{10}$)— (where m is 0 to 2);

R$^1$ is —C(NH)NH$_2$, —C(NH)N(H)OR$^{11}$, —C(NH)N(H)C(O)R$^9$, or —C(NH)N(H)C(O)OR$^{11}$;

R$^2$ and R$^3$ are the same or different and are selected from the group consisting of hydrogen, halo, lower alkyl, lower haloalkyl, aryl, —OR$^{11}$, —C(O)OR$^{11}$, —C(O)N(R$^{11}$)R$^{11}$) R$^{12}$, —N(R$^{11}$)R$^{12}$, —N(H)C(O)R$^{11}$, and —N(H)S(O)$_2$R$^{11}$;

R$^4$ is halo, lower haloalkyl, imidazolyl, —C(NH)NH$_2$, —C(NH)N(H)OR$^{11}$, —C(NH)N(H)C(O)R$^9$, —C(NH)N(H)C(O)OR$^{11}$, —OR$^{11}$, —C(O)R$^{13}$, —(CH$_2$)$_n$C(O)OR$^{11}$ (where n is 0 to 6), —C(O)N(R$^{11}$)R$^{12}$, or —N(R$^{11}$)R$^{12}$;

R$^5$, R$^6$, R$^9$ and R$^{10}$ are independently hydrogen, halo, lower alkyl, lower haloalkyl, 4-pyridinyl, —OR$^{11}$, —C(O) OR$^{11}$, —C(O)N(R$^{11}$)R$^{12}$, or aryl (optionally substituted by one or more substituents selected from the group consisting of halo, hydroxy, lower alkyl, lower haloalkyl, lower alkoxy and —N(R$^{11}$)R$^{12}$);

R$^7$ and R$^8$ are independently hydrogen, lower alkyl, lower haloalkyl, 4-pyridinyl, —C(O)OR$^{11}$, —C(O)N(R$^{11}$)R$^{12}$, or aryl (optionally substituted by one or more substituents selected from the group consisting of halo, hydroxy, lower alkyl, lower haloalkyl, lower alkoxy and —N(R$^{11}$)R$^{12}$);

R$^{11}$ and R$^{12}$ are independently hydrogen, lower alkyl, aryl or lower aralkyl; or R$^{13}$ is pyrrolidinyl, 4-morpholinyl, piperazinyl, N-methylpiperazinyl, or piperidinyl; or a pharmaceutically acceptable salt thereof.

In another aspect, this invention provides compositions useful in treating a human having a disease-state characterized by thrombotic activity, which composition comprises a therapeutically effective amount of a compound of the invention as described above, or a pharmaceutically acceptable salt thereof, and a pharmaceutically acceptable excipient.

In another aspect, this invention provides a method of treating a human having a disease-state characterized by thrombotic activity, which method comprises administering to a human in need thereof a therapeutically effective amount of a compound of the invention as described above.

In another aspect, this invention provides a method of treating a human having a disease-state alleviated by the inhibition of factor Xa, which method comprises administering to a human in need thereof a therapeutically effective amount of a compound of the invention as described above.

In another aspect, this invention provides a method of treating a human having a disease-state alleviated by the inhibition of factor IIa (thrombin), which method comprises administering to a human in need thereof a therapeutically effective amount of a compound of the invention as described above.

In another aspect, this invention provides a method of inhibiting human factor Xa in vitro or in vivo by the administration of a compound of the invention.

In another aspect, this invention provides a method of inhibiting human factor IIa (thrombin) in vitro or in vivo by the administration of a compound of the invention.

DETAILED DESCRIPTION OF THE INVENTION

Definitions

As used in the specification and appended claims, unless specified to the contrary, the following terms have the meaning indicated:

"Halo" refers to bromo, chloro or fluoro.

"Lower alkyl" refers to a straight or branched chain monovalent radical consisting solely of carbon and hydrogen, containing no unsaturation and having from one to four carbon atoms, e.g., methyl, ethyl, n-propyl, 1-methylethyl (iso-propyl), n-butyl, 1,1-dimethylethyl (t-butyl), and the like.

"Lower alkoxy" refers to a radical of the formula —OR$_a$ where R$_a$ is lower alkyl as defined above, e.g., methoxy, ethoxy, t-butoxy, and the like.

"Lower haloalkyl" refers to a lower alkyl radical, as defined above, that is substituted by one or more halo radicals, as defined above, e.g., trifluoromethyl, difluoromethyl, trichloromethyl, 2-trifluoroethyl, 1-fluoromethyl-2-fluoroethyl, 3-bromo-2-fluoropropyl, 1-bromomethyl-2-bromoethyl, and the like.

"Aryl" refers to the phenyl or naphthyl radical.

"Aralkyl" refers to a radical of the formula —R$_a$R$_b$ where R$_a$ is lower alkyl as defined above and R$_b$ is aryl as defined above, e.g., benzyl.

"Amidino" refers to the radical —C(NH)—NH$_2$.

"Benzamidine" refers to a phenyl radical substituted by an amidino radical.

"Naphthamidine" refers to a naphthyl radical substituted by an amidino radical.

"4-pyridinyl" refers to a pyridinyl radical attached at the 4-position.

"Factor IIa" refers to thrombin.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethamine, dicyclohexylamine, choline and caffeine.

"Therapeutically effective amount" refers to that amount of a compound of formula (I) which, when administered to a human in need thereof, is sufficient to effect treatment, as defined below, for disease-states alleviated by inhibition of factor Xa or factor IIa. The amount of a compound of formula (I) which constitutes a "therapeutically effective amount" will vary depending on the compound, the disease-state and its severity, and the age of the human to be treated, but can be determined routinely by one of ordinary skill in the art having regard to his own knowledge and to this disclosure.

"Treating" or "treatment" as used herein cover the treatment of a disease-state in a human, which disease-state is alleviated by inhibition of factor Xa or by factor IIa; and include:

(i) preventing the disease-state from occurring in a human, in particular, when such human is predisposed to the disease-state but has not yet been diagnosed as having it;

(ii) inhibiting the disease-state, i.e., arresting its development; or (iii) relieving the disease-state, i.e., causing regression of the disease-state.

The yield of each of the reactions described herein is expressed as a percentage of the theoretical yield.

The compounds of the invention, or their pharmaceutically acceptable salts, may have asymmetric carbon atoms in their structure. The compounds of the invention and their pharmaceutically acceptable salts may therefore exist as single stereoisomers, racemates, and as mixtures of enantiomers and diastereomers. All such single stereoisomers, racemates and mixtures thereof are intended to be within the scope of this invention.

It is understood, for the purposes of this invention, that the compounds of the invention do not include any combination of substituents that may result in unstable compounds.

The nomenclature used herein for the compounds of the invention is basically a modified form of the I.U.P.A.C. system, wherein the compounds are named as derivatives of benzamidine or naphthamidine. Accordingly, a compound of the invention selected from formula (III), i.e.,

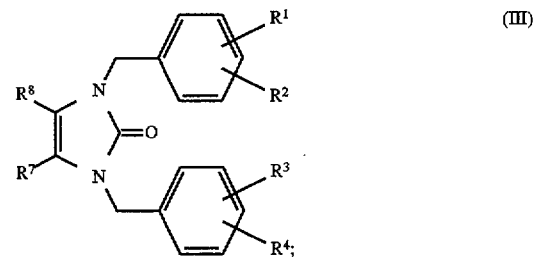

wherein $R^1$ and $R^4$ are both —C(NH)NH$_2$; $R^2$ and $R^3$ are both hydrogen; $R^7$ and $R^8$ are both phenyl; for example, a compound of the following formula:

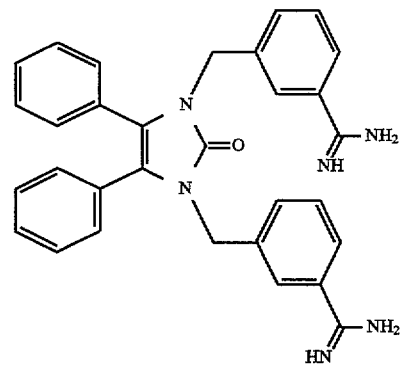

is named herein as 3,3'-[(2,3-dihydro-4,5-diphenyl-2-oxo-1H-imidazol-1,3-diyl)bis(methylene)]bis(benzamidine).

Utility and Administration

A. Utility

The compounds of the invention are inhibitors of factor Xa and factor IIa and therefore useful as anti-coagulants in treating disease-states characterized by thrombotic activity based on factor Xa's or factor IIa's role in the coagulation cascade (see Background of the Invention above). A primary indication for the compounds is prophylaxis for long term risk following myocardial infarction. Additional indications are prophylaxis of deep vein thrombosis (DVT) following orthopedic surgery or prophylaxis of selected patients following a transient ischemic attack. The compounds of the invention may also be useful for indications in which coumadin is currently used, such as for DVT or other types of surgical intervention such as coronary artery bypass graft and percutaneous transluminal coronary angioplasty. The compounds are also useful for the treatment of thrombotic complications associated with acute promyelocytic leukemia, diabetes, multiple myelomas, disseminated intravascular coagulation associated with septic shock, purpura fulminanas associated infection, adult respiratory distress syndrome, unstable angina, and thrombotic complications associated with aortic valve or vascular prosthesis. The compounds are also useful for prophylaxis for thrombotic diseases, in particular in patients who have a high risk of developing such disease.

In addition, the compounds of the invention are useful as in vitro diagnostic reagents for inhibiting factor Xa or factor IIa in the coagulation cascade.

B. Testing

The primary bioassays used to demonstrate the inhibitory effect of the compounds of the invention on factor Xa or factor IIa are simple chromogenic assays involving only serine protease, the compound of the invention to be tested, substrate and buffer (see, e.g., *Thrombosis Res.* (1979), Vol. 16, pp. 245–254). For example, four tissue human serine proteases can be used in the primary bioassay, free factor Xa, prothrombinase, thrombin (factor IIa) and tissue plasminogen activator (tPA). The assay for tPA has been successfully used before to demonstrate undesired side effects in the inhibition of the fibrinolytic process (see, e.g., *J. Med. Chem.* (1993), Vol. 36, pp. 314–319).

Another bioassay useful in demonstrating the utility of the compounds of the invention in inhibiting factor Xa demonstrates the potency of the compounds against free factor Xa in citrated plasma. For example, the anticoagulant efficacy of the compounds of the invention will be tested using either the prothrombin time (PT), or activated partial thromboplastin time (aPTT) while selectivity of the compounds is checked with the thrombin clotting time (TCT) assay. Correlation of the $K_i$ in the primary enzyme assay with the $K_i$ for free factor Xa in citrated plasma will screen against compounds which interact with or are inactivated by other plasma components. Correlation of the $K_i$ with the extension of the PT is a necessary in vitro demonstration that potency in the free factor Xa inhibition assay translates into potency in a clinical coagulation assay. In addition, extension of the PT in citrated plasma can be used to measure duration of action in subsequent pharmacodynamic studies.

For further information on assays to demonstrate the activity of the compounds of the invention, see R. Lottenberg et al., *Methods in Enzymology* (1981), Vol. 80, pp. 341–361, and H. Ohno et al., *Thrombosis Research* (1980), Vol. 19, pp. 579–588.

C. General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally, topically, transdermally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. The compositions will include a conventional pharmaceutical carrier or excipient and a compound of the invention as the/an active agent, and, in addition, may include other medicinal agents, pharmaceutical agents, carriers, adjuvants, etc.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. Preferably, the composition will be about 5% to 75% by weight of a compound(s) of the invention, or a pharmaceutically acceptable salt thereof, with the rest being suitable pharmaceutical excipients.

The preferred route of administration is oral, using a convenient daily dosage regimen which can be adjusted according to the degree of severity of the disease-state to be treated. For such oral administration, a pharmaceutically acceptable composition containing a compound(s) of the invention, or a pharmaceutically acceptable salt thereof, is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such compositions take the form of solutions, suspensions, tablets, pills, capsules, powders, sustained release formulations and the like.

Preferably such compositions will take the form of capsule, caplet or tablet and therefore will also contain a diluent such as lactose, sucrose, dicalcium phosphate, and the like; a disintegrant such as croscarmellose sodium or derivatives thereof; a lubricant such as magnesium stearate and the like; and a binder such as a starch, gum acacia, polyvinylpyrrolidone, gelatin, cellulose ether derivatives, and the like.

The compounds of the invention, or their pharmaceutically acceptable salts, may also be formulated into a suppository using, for example, about 0.5% to about 50% active ingredient disposed in a carrier that slowly dissolves within the body, e.g., polyoxyethylene glycols and polyethylene glycols (PEG), e.g., PEG 1000 (96%) and PEG 4000 (4%).

Liquid pharmaceutically administrable compositions can, for example, be prepared by dissolving, dispersing, etc., a compound(s) of the invention (about 0.5% to about 20%), or a pharmaceutically acceptable salt thereof, and optional pharmaceutical adjuvants in a carrier, such as, for example, water, saline, aqueous dextrose, glycerol, ethanol and the like, to thereby form a solution or suspension.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Actual methods of preparing such dosage forms are known, or will be apparent, to those skilled in this art; for example, see *Remington's Pharmaceutical Sciences*, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state alleviated by the inhibition of factor Xa in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. Generally, a therapeutically effective daily dose is from about 0.14 mg to about 14.3 mg/kg of body weight per day of a compound of the invention, or a pharmaceutically acceptable salt thereof; preferably, from about 0.7 mg to about 10 mg/kg of body weight per day; and most preferably, from about 1.4 mg to about 7.2 mg/kg of body weight per day. For example, for administration to a 70 kg person, the dosage range would be from about 10 mg to about 1.0 gram per day of a compound of the invention, or a pharmaceutically acceptable salt thereof, preferably from about 50 mg to about 700 mg per day, and most preferably from about 100 mg to about 500 mg per day.

Preferred Embodiments

Of the compounds of the invention as set forth above in the Summary of the Invention, several groups of compounds are preferred.

One preferred group is that group of compounds selected from formula (I) wherein $R^1$ is —C(NH)NH$_2$, —C(NH)N(H)OR$^{11}$ or —C(NH)N(H)C(O)OR$^{11}$; $R^2$ and $R^3$ are each hydrogen; $R^4$ is —C(NH)NH$_2$, —C(NH)N(H)OR$^{11}$ or —C(NH)N(H)C(O)OR$^{11}$; $R^5$, $R^6$, $R^9$ and $R^{10}$ are independently hydrogen, halo, or lower alkyl; and $R^{11}$ is hydrogen, lower alkyl, aryl or lower aralkyl.

Of this group of compounds, a preferred subgroup are those compounds wherein $R^1$ and $R^4$ are each —C(NH)NH$_2$; and $R^5$, $R^6$, $R^9$ and $R^{10}$ are independently hydrogen or halo.

Of this subgroup of compounds, a preferred class of compounds are those compounds wherein $R^5$, $R^6$, $R^9$ and $R^{10}$ are each chloro.

A preferred compound of this subgroup is 3,3'-[(1,2-dihydro-2-oxo-4,5,6,7-tetrachloro-1H-benzimidazol-1,3-diyl)bis(methylene)]bis(benzamidine).

Another preferred group of compounds is that group of compounds selected from the formula (III) wherein $R^1$ is —C(NH)NH$_2$, —C(NH)N(H)OR$^{11}$ or —C(NH)N(H)C(O)OR$^{11}$; $R^2$ and $R^3$ are independently hydrogen, lower alkyl or —OR$^{11}$; $R^4$ is —C(NH)NH$_2$, —C(NH)N(H)OR$^{11}$, —C(NH)C(H)C(O)OR$^{11}$, or —C(O)N(R$^{11}$)R$^{12}$; $R^7$ and $R^8$ are independently hydrogen, lower alkyl, or aryl (optionally substituted by one or substituents selected from the group consisting of halo, hydroxy, lower alkyl, lower haloalkyl, lower alkoxy and —N(R$^{11}$)R$^{12}$); and $R^{11}$ and $R^{12}$ are independently hydrogen, lower alkyl, phenyl or benzyl.

Of this group of compounds, a preferred subgroup of compounds is that subgroup wherein $R^1$ is —C(NH)NH$_2$; $R^2$ and $R^3$ are independently hydrogen or —OR$^{11}$; $R^4$ is —C(NH)NH$_2$ or —C(O)N(R$^{11}$)R$^{12}$; $R^7$ and $R^8$ are independently hydrogen, lower alkyl or phenyl (optionally substituted by one or more substituents selected from the group consisting of —OR$^{11}$ and —N(R$^{11}$)R$^{12}$); and $R^{11}$ and $R^{12}$ are independently hydrogen or lower alkyl.

Of this subgroup of compounds, a preferred class of compounds is that class wherein $R^1$ and $R^4$ are both —C(NH)NH$_2$; $R^2$ and $R^3$ are both hydrogen; $R^7$ and $R^8$ are independently phenyl optionally substituted by —OR$^{11}$ or —N(R$^{11}$)R$^{12}$; and $R^{11}$ and $R^{12}$ are independently hydrogen or lower alkyl.

Of this class of compounds a preferred subclass is that subclass of compounds wherein $R^7$ and $R^8$ are both phenyl.

Of this subclass of compounds, a preferred compound is 3,3'-[(2,3-dihydro-4,5-diphenyl-2-oxo-1H-imidazol-1,3-diyl)bis(methylene)]bis(benzamidine).

Another preferred subclass of compounds from this class is that subclass of compounds wherein $R^7$ is phenyl; and $R^8$ is 4-dimethylaminophenyl.

Of this subclass of compounds, a preferred compound is 3,3'-[[2,3-dihydro-4-(4-dimethylaminophenyl)-2-oxo-5-phenyl-1H-imidazol-1,3-diyl]bis(methylene)]-bis(benzamidine).

Another preferred group of compounds is that group selected from formula (IV) wherein $R^1$ and $R^4$ are both —C(NH)NH$_2$; $R^2$ and $R^3$ are independently hydrogen or —OR$^{11}$; $R^7$, $R^8$ and $R^9$ are independently hydrogen, lower alkyl or phenyl (optionally substituted by one or more substituents selected from the group consisting of —OR$^{11}$ and —N(R$^{11}$)R$^{12}$); and $R^{11}$ and $R^{12}$ are independently hydrogen or lower alkyl.

Of this group of compounds, a preferred subgroup of compounds is that subgroup wherein $R^1$ and $R^4$ are both —C(NH)NH$_2$; $R^2$ and $R^3$ are both hydrogen; both phenyl; and $R^9$ is hydrogen.

Preferred compounds of this subgroup are 7-[[3-[4-(amidino)benzyl]-2,3-dihydro-4,5-diphenyl-2-oxo-1H-imidazol-1-yl]methyl]-naphthalene-2-carboximidamide and 7-[[3-[3-(amidino)benzyl]-2,3-dihydro-4,5-diphenyl-2-oxo-1H-imidazol-1-yl]methyl]naphthalene-2-carboximidamide.

Another preferred group of compounds is that group selected from formula (V) wherein $R^1$ and $R^4$ are both —C(NH)NH$_2$; $R^2$ and $R^3$ are independently hydrogen or —OR$^{11}$; $R^7$, $R^8$, $R^9$ and $R^{10}$ are independently hydrogen, lower alkyl or phenyl (optionally substituted by one or more substituents selected from the group consisting of —OR$^{11}$ and —N(R$^{11}$)R$^{12}$); and $R^{11}$ and $R^{12}$ are independently hydrogen or lower alkyl.

Of this group, a preferred subgroup of compounds is that subgroup wherein $R^1$ and $R^4$ are both —C(NH)NH$_2$; $R^2$ and $R^3$ are both hydrogen; $R^7$ and $R^8$ are both phenyl; and $R^9$ and $R^{10}$ are both hydrogen.

A preferred compound of this subgroup is 7,7'-[[2,3-dihydro-4,5-diphenyl-2-oxo-1H-imidazol-1,3-diyl]bis(methylene)]bis(naphthalene-2-carboximidamide).

Preparation of Compounds of the Invention

As a matter of convenience, the following description of the preparation of the compounds of the invention is directed to the preparation of compounds of formula (III), although similar reagents and reaction conditions may be used to produced the other compounds of the invention.

A. Starting Materials

Compounds of formula (B) are starting materials in the prepration of the compounds of the invention and are commercially available or may be prepared according to methods known to those skilled in the art, or may be prepared as illustrated below in Reaction Scheme 1 wherein $R^{14}$ and $R^{15}$ are independently hydrogen or arylmethyl (where the aryl group is substituted by a cyano group and optionally substituted by one or more substituents selected from the group consisting of halo, lower alkyl, lower haloalkyl, —OR$^{11}$, —C(O)OR$^{11}$, —C(O)N(R$^{11}$)R$^{12}$, —N(R$^{11}$)R$^{12}$, —N(H)C(O)R$^{11}$, or —N(H)S(O)$_2$R$^{11}$ where $R^{11}$ and $R^{12}$ are independently hydrogen, lower alkyl, aryl or lower aralkyl):

Reaction Scheme 1

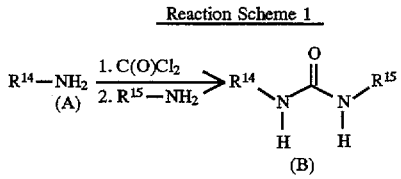

Compounds of formula (A) are commercially available, for example, from Aldrich Chemical Co., Inc., or made by prepared by methods known to those of ordinary skill in the art.

In general, compounds of formula (B) are prepared by reacting a compound of formula (A) with COCl$_2$ (phosgene) or a phosgene equivalent under basic conditions, such as utilizing triethylamine under standard conditions to form the intermediate, [R$^{14}$—N(H)=C=O], which is then reacted with a compound of formula R$^{15}$—NH$_2$ under standard conditions to form a compound of formula (B).

B. Intermediates

1. Compounds of formula (Da) are intermediates in the preparation of the compounds of the invention. They are prepared from compounds of formula (C) and formula (B) as illustrated below in Reaction Scheme 2 where $R^7$ and $R^8$ are independently lower alkyl, lower haloalkyl, 4-pyrdinyl or aryl (optionally substituted by one or more substituents selected from the group consisting of halo, hydroxy, lower alkyl, lower haloalkyl, lower alkoxy and —$N(R^{11})R^{12}$ wher $R^{11}$ and $R^{12}$ are independently hydrogen, lower alkyl, aryl or lower aralkyl); and $R^{14}$ and $R^{15}$ are independently hydrogen or arylmethyl (where the aryl group is substituted by cyano and optionally substituted by one or more substituents selected from the group consisting of halo, lower alkyl, lower haloalkyl, —$OR^{11}$, —$C(O)OR^{11}$, —$C(O)N(R^{11})R^{12}$, —$N(R^{11})R^{12}$, —$N(H)C(O)R^{11}$ or —$N(H)S(O)_2R^{11}$ (where $R^{11}$ and $R^{12}$ are independently hydrogen, lower alkyl, aryl or lower aralkyl)):

Reaction Scheme 2

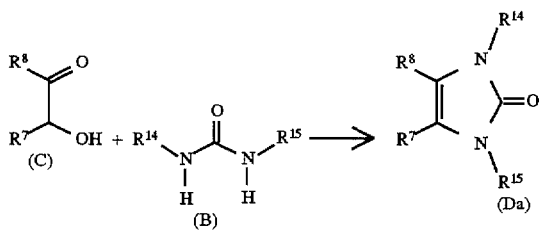

Compounds of formula (C) may be commercially available or prepared from the appropriate compounds, such as aldehydes, according to methods known to those of ordinary skill in the art.

In general, a compound of formula (Da) are prepared by reacting a compound of formula (C) with a compound of formula (B) under acidic conditions, such as in refluxing acetic acid. The compound of formula (Da) is then isolated from the reaction mixture by standard techniques, such as crystallization or chromatography.

2. Compounds of formula (Fa) are also intermediates in the preparation of the compounds of the invention. They are prepared from compounds of formula (Db), and from formula (E) as illustrated below in Reaction Scheme 3 where X is chloro, bromo or iodo; $R^2$ is hydrogen, halo, lower alkyl, lower haloalkyl, aryl, —$OR^{11}$, —$C(O)OR^{11}$, —$N(R^{11})R^{12}$, —$N(H)C(O)R^{11}$ or —$N(H)S(O)_2R^{11}$; $R^3$ is hydrogen, halo, lower alkyl, lower haloalkyl, aryl, or —$OR^{11}$; $R^7$ and $R^8$ are independently hydrogen, lower alkyl, lower haloalkyl, —$C(O)OR^{11}$, —$C(O)N(R^{11})R^{12}$, or aryl (optionally substituted by one or more substituents selected from the group consisting of halo, —$OR^{11}$, lower alkyl, lower haloalkyl and —$N(R^{11})R^{12}$); where each $R^{11}$ and $R^{12}$ are independently hydrogen, lower alkyl, aryl or lower aralkyl:

Reaction Scheme 3

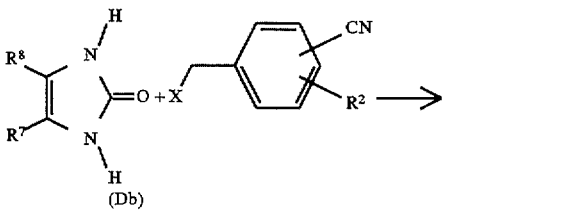

-continued
Reaction Scheme 3

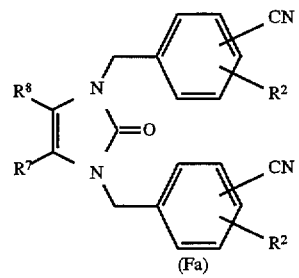

Compounds of formula (Db) may be prepared according to the method described in Reaction Scheme 2 above for a compound of formula (Da) where $R^{14}$ and $R^{15}$ are hydrogen, or by methods known to those of ordinary skill in the art. Compounds of formula (E) may be commercially available or prepared by methods known to those of ordinary skill in the art.

In general, a compound of formula (Fa) are prepared by reacting a compound of formula (Db) with two or more molar equivalent mounts of a compound of formula (E) under standard alkylation conditions to prepare a compound of formula (Fa). The compound of formula (Fa) is then isolated from the reaction mixture by standard techniques, such as crystallization or chromatography.

3. Compounds of formula (L) are also intermediates in the preparation of compounds of the invention. They are prepared as illustrated below in Reaction Scheme 4 wherein X is bromo, chloro, iodo; $R^2$ is hydrogen, halo, lower alkyl, lower haloalkyl, aryl, —$OR^{11}$, —$C(O)OR^{11}$, —$N(R^{11})R^{12}$, —$N(H)C(O)R^{11}$ or —$N(H)S(O)_2R^1$; $R^7$ and $R^8$ are independently hydrogen, lower alkyl, lower haloalkyl, —$C(O)OR^{11}$, —$C(O)N(R^{11})R^{12}$, or aryl (optionally substituted by one or more substituents selected from the group consisting of halo, —$OR^{11}$, lower alkyl, lower haloalkyl and —$N(R^{11})$ R12), where each $R^{11}$ and $R^{12}$ are independently hydrogen, lower alkyl, aryl or lower aralkyl; and each $R^{16}$ is lower alkyl, aryl or lower aralkyl:

Reaction Scheme 4

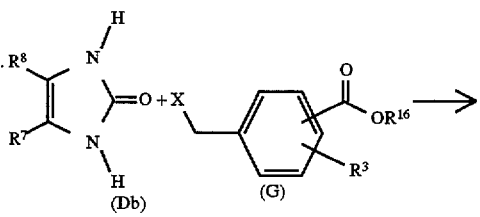

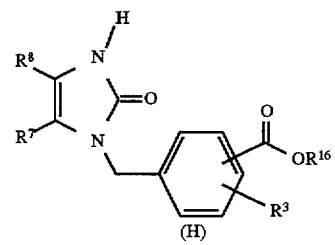

13

-continued
Reaction Scheme 4

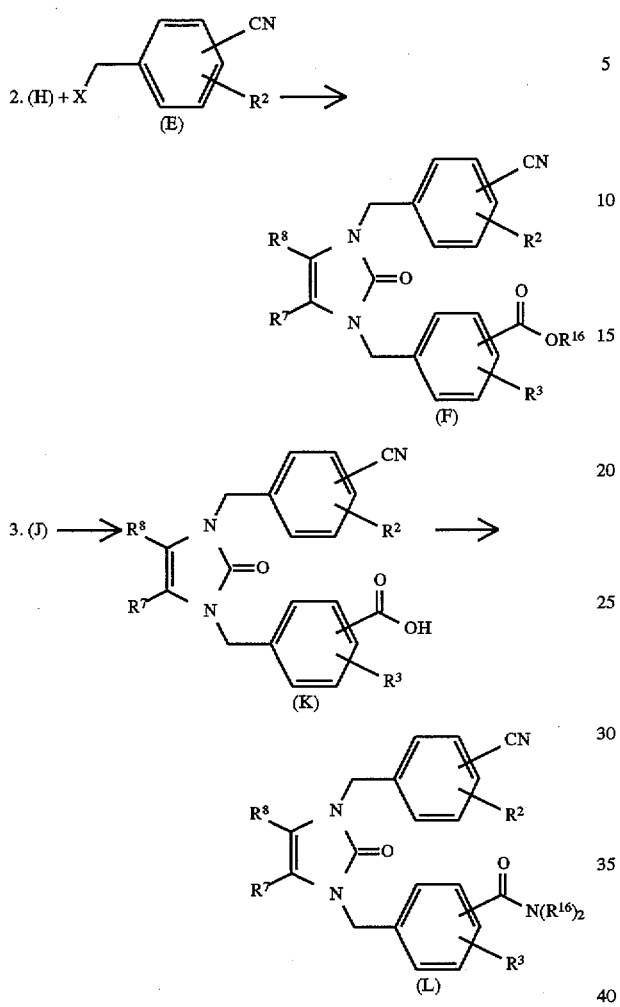

Compounds of formula (Db) may be prepared according to the method described in Reaction Scheme 2 above, or by methods known to those of ordinary skill in the art.

Compounds of formula (G) and formula (E) may be commercially available or prepared by methods known to those of ordinary skill in the art.

In general, compounds of formula (L) are prepared by first treating a compound of formula (Db) with a compound of formula (G) as a limiting reagent under standard alkylation conditions, for example, in an aprotic solvent in the presence of a base such as sodium hydride at temperatures between about 20° C. to about 50° C., preferably at about 50° C., to yield a compound of formula (H). The compound of formula (H) is then treated with one molar equivalent amount of a compound of formula (E) under similar alkylation condtions, to yield a compound of formula (J). The compound of formula (J) is then hydrolyzed under standard basic hydrolysis conditions to yield a compound of formula (K), which is then treated with the appropriate amine under standard conditions to yield a compound of formula (L).

C. Preparation of the Compounds of the Invention

The following Reaction Scheme is illustrative of the preparation of compounds of the invention, particularly those of formula (III) as described above in the Summary of the Invention, but similar reagents and reaction conditions may be used to prepared compounds of the other formulae.

14

Compounds of formula (IIIa) are compounds of the invention and are prepared as described below in Reaction Scheme 5 wherein $R^2$, $R^3$, $R^7$ and $R^8$ are the same as described above in the Summary of the Invention:

Reaction Scheme 5

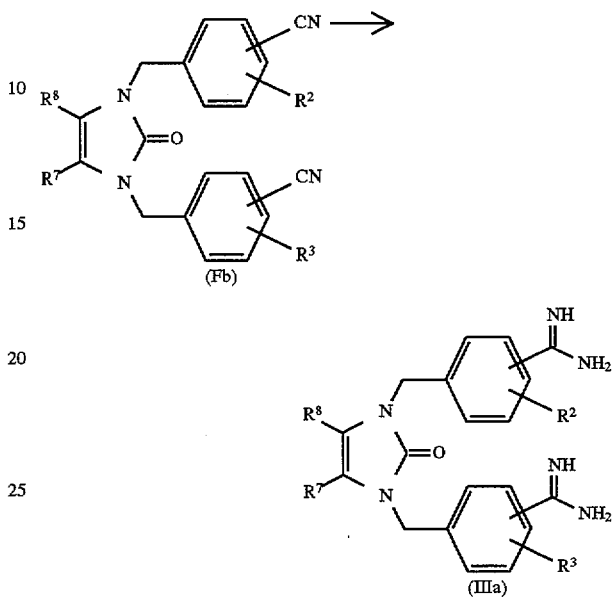

Compounds of formula (Fb) may be prepared according to the methods described above for compounds of formula (Fa).

In general, a compound of formula (IIIa) is prepared by first dissolving a compound of formula (Fb) in a lower alkanol, preferably ethanol, and then treating the solution overnight at around 0° C. with an anhydrous mineral acid, preferably HCl. The solvent is then removed and the resulting residue dissolved in fresh lower alkanol, preferably ethanol. The resulting solution is then treated with anhydrous ammonia at temperatures from between ambient temperatures and 100° C. from about 1 to about 5 hours. The above reactions are carried out in high-pressure glass tubes and vessels. The compound of formula (IIIa) is then isolated from the reaction mixture by standard techniques.

In the following Reaction Scheme, compounds of formula (IIIb), which are also compounds of the invention, are similarly prepared from compounds of formual (L), as illustrated below in Reaction Scheme 6, where $R^2$, $R^4$, $R^7$ and $R^8$ are as described above in the Summary of the Invention:

Reaction Scheme 6

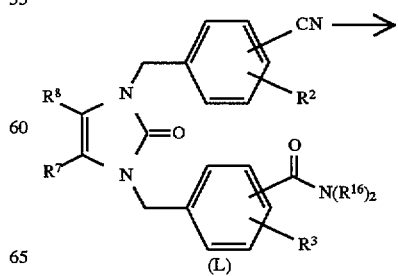

-continued
Reaction Scheme 6

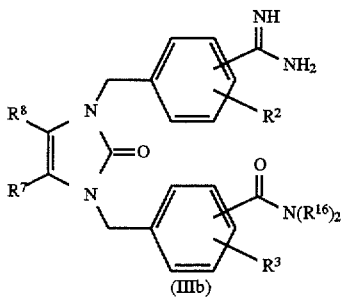

(IIIb)

Compounds of formula (L) may be prepared according to the methods described above in Reaction Scheme 4.

Compounds of formulae (IIIa) and (IIIb) wherein $R^7$ or $R^8$ is —C(O)OR$^{11}$ (where $R^{11}$ is lower alkyl) may be further hydrolyzed to produce compounds of the invention where $R^7$ or $R^8$ is C(O)OR$^{11}$ where $R^{11}$ is hydrogen. Such compounds may be further amidated to produce compounds of the invention wherein $R^7$ or $R^8$ are —C(O)N(R$^{11}$)R$^{12}$ (where $R^{11}$ and $R^{12}$ are hydrogen, lower alkyl, aryl or lower aralkyl).

Compounds of formulae (IIIa) and (IIIb) may be further treated with acid halides, preferably acid chlorides, or with acid anhydrides or equivalents, to yield compounds of the invention where $R^1$ and $R^4$ are —C(NH)N(H)C(O)R$^{11}$. Alternatively, compounds of formulae (IIIa) and (IIIb) may be further treated with carbamoyl chlorides, or their equivalents, to yield compounds of the invention where $R^1$ and $R^4$ are —C(NH)N(H)C(O)OR$^{11}$.

Compounds of the invention (as described above in the Summary of the Invention) wherein $R^1$ or $R^4$ are —C(NH)N(H)OR$^{11}$ are prepared by treating a compound of formulae (Fa), (Fb), (J), (K) and (L), as described above, with hydroxylamines of the formula $R^{11}$ONH$_2$ (where $R^{11}$ is as described above in the Summary of the Invention) under basic conditions, preferably in the presence of triethylamine.

In summary, compounds of the invention, as illustrated above by the preparation of compounds of formula (III), are prepared by:

(1) treating a compound of formula (C) with a compound of formula (B) to yield a compound of formula (Da); or
(2) treating a compound of formula (Db) with a compound of formula (E) to yield a compound of formula (Fa); or
(3) treating a compound of formula (Db) with a compound of formula (G) to yield a compound of formula (H); and then treating the compound of formula (H) with a compound of formula (E) to yield a compound of formula (J); and then treating the compound of formula (J) to yield a compound of formula (K) ; and then treating the compound of formula (K) to yield a compound of formula (L); and
(4) treating a compound of formulae (Da), (L) , (Fa) or (Fb) to form a compound of formula (III).

In addition, all compounds of the invention that exist in free base form or free acid form may be converted to their pharmaceutically acceptable salts by treatment with the appropriate inorganic or organic acid, or by the appropriate inorganic or organic base by methods known to those of ordinary skill in the art. Salts of the compounds of the invention can also be converted to the free base form or to the free acid form or to another salt by known methods.

The following specific preparations and examples are provided as a guide to assist in the practice of the invention, and are not intended as a limitation on the scope of the invention.

PREPARATION 1

4,4'-[(2-Oxoimidazolin-1,3-diyl)bis(methylene)]bis (benzonitrile).

A. To sodium hydride (2.4 g, 60 mmol) in dimethylformamide (50 mL) at 0° C. was added imidazolin-2-one (2.6 g, 30 mmol). After stirring for 20 minutes 4-(bromomethyl) benzonitrile (13 g, 66 mmol) was added and the mixture was warmed to ambient temperature. After stirring for 1 hour the reaction was poured into water and a solid formed. The solid was filtered to give 4,4'-[(2-oxoimidazolin-1,3-diyl)bis (methylene)]-bis(benzonitrile). NMR (CDCl$_3$) 7.65 (d,4), 7.4 (d,4), 4.45 (s,4), 3.2 (s,4) ppm.

B. In a similar manner, the following compounds were made:

4,4'-[(1,2,3,4,5,6-hexahydro-2-oxopyrimidin-1,3-diyl)bis (methylene)]bis(benzonitrile); NMR (CDCl$_3$) 7.63 (d,4), 7.4 (d,4), 3.25 (m,4), 4.62 (s,4), 3.25 (m,4), 1.97 (m,2) ppm;

3,3'-[(2-oxoimidazolin-1,3-diyl)bis(methylene)]bis (benzonitrile); NMR (CDCl$_3$) 7.6 (m,6), 7.47 (m,2), 4.45 (s,4), 3.23 (s,4) ppm;

3,3'-[(2-oxo-4,4,5,5-tetramethylimidazolin-1,3-diyl)bis (methylene)]bis(benzonitrile); NMR (CDCl$_3$) 7.62 (m,4), 7.55 (d,2), 7.44 (t,2), 4.38 (s,4), 1.05 (s,12) ppm;

4,4'-[(2-oxo-4,4,5,5-tetramethylimidazolin-1,3-diyl)bis (methylene)]bis(benzonitrile); NMR (CDCl$_3$) 7.65 (d,4), 7.55 (d,4), 4.4 (s,4), 1.1 (s,12) ppm;

1,3-bis(3-cyanobenzyl)-1,2-dihydro-5-ethyl-2-oxo-1H-imidazole-4-carboxylic acid, methyl ester; NMR (CDCl$_3$) 7.4–7.7 (m,8), 5.3 (s,2), 5.0 (s,2), 3.79 (s,3), 2.7 (q,2), 1.04 (t,3) ppm;

1,3-bis(3-cyanobenzyl)-1,2-dihydro-2-oxo-1H-imidazole-4, 5-dicarboxylicacid, diethyl ester; NMR (CDCl$_3$) 7.6 (m,6), 7.45 (m,2), 5.15 (s,4), 4.24 (q,4), 1.25 (t,6) ppm;

3,3'-[(2,3-dihydro-4-methyl-2-oxo-5-phenyl-1H-imidazol-1,3-diyl)bis(methylene)]-bis(benzonitrile); NMR (CDCl$_3$) 7.1–7.6 (m, 13), 5.0 (s,2), 4.87 (s,2), 1.95 (s,6) ppm;

3,3'-[(2,3-dihydro-4-ethyl-2-oxo-5-phenyl-1H-imidazol-1, 3-diyl)bis(methylene)]-bis(benzonitrile); NMR (CDCl$_3$) 7.5–7.7 (m,4), 7.3–7.5 (m,6), 7.2 (s,1), 7.15 (m,2), 5.02 (s,2), 4.83 (s,2), 2.3 (q,2), 0.95 (t,6) ppm;

3,3'-[(4,5-bis(methylethyl)-2,3-dihydro-2-oxo-1H-imidazol-1,3-diyl)bis(methylene)]-bis(benzonitrile); NMR (CDCl$_3$) 7.56 (m,2), 7.5 (m,8), 5.03 (s,4), 2.95 (m,2), 1.13 (d,12) ppm;

3,3'-[(4,5-diethyl-2,3-dihydro-2-oxo-1H-imidazol-1,3-diyl) bis(methylene)]-bis(benzonitrile); NMR (CDCL$_3$) 7.6 (m,2), 7.58 (m,8), 4.95 (s,4), 2.3 (q,4), 1.0 (t,6) ppm; and 3,3'-[(2,3-dihydro-4,5-dimethyl-2-oxo-1H-imidazol-1,3-diyl)bis(methylene)]-bis(benzonitrile); NMR (CDCl$_3$) 7.6 (m,2), 7.5 (m,8), 4.93 (s,4), 1.9 (s,6) ppm.

PREPARATION 2

4,4'-[(1,2-Dihydro-2-oxo-1H-benzimidazol-1,3-diyl) bis(methylene)]bis(benzonitrile)

A. To dimethylformamide (50 mL) was added 2-hydroxy-1H-benzimidazole (2.7 g, 25 mmol), cesium carbonate (17 g, 55 mmol), and 4-(bromomethyl)benzonitrile (10 g, 50 mmol). After stirring for 3 hours, the mixture was poured into water. The precipitate was filtered and washed with water. The solid was dissolved in ethyl acetate, dried ($Na_2SO_4$), treated with charcoal, and the solvent was removed in vacuo to give 4,4'-[(1,2-dihydro-2-oxo-1H-benzimidazol-1,3-diyl)bis(methylene)]bis(benzonitrile); NMR ($CDCl_3$) 7.85 (d,4), 7.6 (d,4), 7.2 (m,2), 7.1 (m,2), 5.25 (s,4) ppm.

B. In a similar manner, the following compounds were made:

3,3'-[(1,2-dihydro-2-oxo-1H-benzimidazol-1,3-diyl)bis (methylene)]bis(benzonitrile); NMR ($CDCl_3$) 7.6 (m,6), 7.48 (m,2), 7.07 (m,2), 6.89 (m,2), 5.15 (s,4) ppm;

4,4'-[(1,2-dihydro-4-methyl-2-oxo-1H-benzimidazol-1,3-diyl)bis(methylene)]-bis(benzonitrile); NMR ($CDCl_3$) 7.65 (d,4), 7.44 (d,2), 7.28 (d,2), 6.95 (t,1), 6.83 (d,1), 6.75 (d,1), 5.4 (s,2), 5.18 (s,2), 2.3 (s,3) ppm;

4,4'-[(1,2-dihydro-4,7-dimethyl-2-oxo-1H-benzimidazol-1, 3-diyl)bis(methylene)]-bis(benzonitrile);

3,3'-[(1,2-dihydro-4-methyl-2-oxo-1H-benzimidazol-1,3-diyl)bis(methylene)]-bis(benzonitrile); NMR ($CDCl_3$) 7.6 (m,4), 7.44 (m,2), 6.98 (t,2), 6.83 (d,1), 6.77 (d, 1), 5.4 (s,2), 5.18 (s,2), 2.33 (s,3) ppm;

3,3'-[(1,2-dihydro-4,7-dimethyl-2-oxo-1H-benzimidazol-1, 3-diyl)bis(methylene)]-bis(benzonitrile); NMR ($CDCl_3$) 7.6 (m,2), 7.45 (m,6), 6.72 (s,2), 5.43 (s,4), 2.33 (s,6) ppm;

3,3'[(5,6-dichloro-1,2-dihydro-2-oxo-1H-benzimidazol-1,3-diyl)bis(methylene)]-bis(benzonitrile);

3,3'-[[2,3-dihydro-4-(4-dimethylaminophenyl)-2-oxo-5-phenyl-1H-imidazol-1,3-diyl]bis(methylene)]bis (benzonitrile); NMR ($CDCl_3$) 7.3–7.6 (m,6), 7.24 (m,5), 7.03 (m,2), 6.85 (d,2), 6.53 (d,2), 4.9 (s,2), 4.86 (s,2), 2.95 (s,6) ppm;

3,3'-[[2,3-dihydro-4,5-bis(4-methoxyphenyl)-2-oxo-1H-imidazol-1,3-diyl]bis(methylene)]-bis(benzonitrile);

7,7'-[(2,3-dihydro-4,5-diphenyl-2-oxo-1H-imidazol-1,3-diyl)bis(methylene)]-bis(naphthalene-2-carbonitrile);

4,4'-[(2,3-dihydro-4,5-diphenyl-2-oxo-1H-imidazol-1,3-diyl)bis(methylene)]-bis(benzonitrile);

3,3'-[(2,3-dihydro-2-oxo-4-phenyl-1H-imidazol-1,3-diyl) bis(methylene)]bis(benzonitrile); NMR ($CDCl_3$) 7.4–7.6 (m,5), 7.24 (m,5), 7.03 (m,3), 6.13 (s,1), 4.85 (s,2), 4.83 (s,2) ppm;

3,3'-[(1,2-dihydro-2-oxo-4,5,6,7-tetrachloro-1H-benzimidazol-1,3-diyl)bis(methylene)]-bis (benzenecarbonitrile); NMR ($CDCl_3$) 7.6 (m,2), 7.48 (m,6), 5.6 (s,4) ppm;

3,3'-[(2,3-dihydro-4,5-diphenyl-2-oxo-1H-imidazol-1,3-diyl)bis(methylene)]-bis(benzonitrile); and 4,4'-[(1,2-dihydro-2-oxo-4,5,6,7-tetrachloro-1H-benzimidazol-1,3-diyl)bis(methylene)]-bis(benzonitrile); NMR ($CDCl_3$) 7.65 (m,4), 7.33 (m,4), 5.6 (s,4) ppm.

PREPARATION 3

4-(4-Dimethylaminophenyl)-2,3-dihydro-5-phenyl-1H-imidazol-2-one

A. To acetic acid (2 mL) was added urea (0.6 g, 10 mmol) and 2-(4-dimethylaminophenyl)-2-hydroxy-1-phenylethanone (2.6 g, 10 mmol). After stirring for 2 hours at 120° C., the reaction was cooled to ambient temperature. The resulting solid was filtered, washed with ether, and dried in vacuo to give 4-(4-dimethylaminophenyl)-2,3dihydro-5-phenyl-1H-imidazol-2-one; NMR ($CDCl_3$) 10.98 (s,2), 7.5 (m,4), 7.4 (m,5), 3.18 (s,6) ppm.

B. In a similar manner, the following compounds were made:

4,5-bis(4-methoxyphenyl)-2,3-dihydro-1H-imidazol-2-one; NMR (DMSO-$d_6$) 11.0 (s,2), 7.62 (d,1), 7.26 (d,4), 6.9 (d,4), 3.73 (s,6) ppm;

2,3-dihydro-4-ethyl-5-phenyl-1H-imidazol-2-one; NMR (DMSO-$d_6$) 11.02 (s, 1), 10.98 (s,1), 7.4 (m,4), 7.3 (m,1), 2.5 (m,2), 1.2 (t,3) ppm; and 4,5-diethyl-2,3-dihydro-1H-imidazol-2-one; NMR (DMSO-d6) 9.5 (s,2), 2.22 (q,4), 1.05 (t,6) ppm.

PREPARATION 4

3-[(2,3-Dihydro-4,5-diphenyl-2-oxo-1H-imidazol-1-yl)methyl]benzonitrile

A. In a manner similar to Preparation 1 above, 2,3-dihydro-4,5-diphenyl-1H-imidazol-2-one (1.2 g, 5 mmol) was reacted with 3-(bromomethyl)benzonitrile (0.39 g, 2 mmol) and sodium hydride (0.18 g, 5 mmol) in dimethylformamide (20 mL) to give 3-[(2,3-dihydro-4,5-diphenyl-2-oxo-1H-imidazol-1-yl)methyl]benzonitrile after chromatography on silica; NMR (DMSO-$d_6$) 11.02 (s,1), 7.4 (m,4), 7.3 (m,2), 7.2 (m,7), 4.75 (s,2) ppm.

B. In a similar manner, the following compound was made:

4-[(2,3-dihydro-4,5-diphenyl-2-oxo-1H-imidazol-1-yl) methyl]benzonitrile; NMR (DMSO-$d_6$) 11.02 (s,1), 7.67 (d,2), 7.4 (m,3), 7.2 (m,9), 4.75 (s,2) ppm.

PREPARATION 5

2-(3-methoxycarbonylphenyl)methyl-dihydro-4,5-diphenyl-1H-imidazol-2-one

A. To 2,3-dihydro-4,5-diphenyl-1H-imidazol-2-one (4.76 g, 20 mmol) in 50 mL DMF was added to a suspension of NaH (0.8 g, 20 mmol) in 25 mL DMF. The suspension was stirred at ambient temperatures for 30 minutes, then heated to 50° C. for 30 minutes. A solution of methyl 3-bromomethylbenzoate (2.86 g, 12.5 mmol) in 20 mL DMF was then added and the reaction stirred for 10 min at 50° C. The mixture was poured into 1N HCl, filtered, washed with water and dried. Chromatography on silica gel (2% EtOH in 7:3 methylene chloride/ethyl acetate) afforded 1.2 g of 3-(3-methoxycarbonylphenyl)methyl-4,5-diphenyl-1H-imidazol-2-one as a white solid.

B. In a similar manner, the following compounds are made:

3-(3-ethoxycarbonylphenyl)methyl-4,5-diphenyl-1H-imidazol-2-one;

3-(3-phenoxycarbonylphenyl)methyl-4,5-diphenyl-1H-imidazol-2-one; and 3-(3-benzyloxycarbonylphenyl)methyl-4,5-diphenyl-1H-imidazol-2-one.

PREPARATION 6

7-[[3-(3—Cyanophenyl)methyl-2,3-dihydro-4,5-diphenyl-2-oxo-1H-imidazol-1-yl]methyl] naphthalene-2-carbonitrile A. In a manner similar to Preparation 2 above, 3-[(2,3-dihydro-4,5-diphenyl-2-oxo-1H-imidazol-1-yl)methyl] benzonitrile was reacted with 7-(bromomethyl)naphthalene-2-carbonitrile to give 7-[[3-(3-cyanophenyl)methyl-2,3- dihydro-4,5-diphenyl-2-oxo-1H-imidazol-1-yl]methyl] naphthalene-2-carbonitrile; NMR (CDCl$_3$) 8.05 (s,1), 7.9 (d,1), 7.85 (d,1), 7.55 (m,3), 7.4 (m,2), 7.2 (m,9), 7.0 (m,3), 5.1 (s,2), 4.95 (s,2) ppm.

B. In a similar manner, the following compounds were made:

7-[[3-(4-cyanophenyl)methyl-2,3-dihydro-4,5-diphenyl-2-oxo-1H-imidazol-1-yl]methyl]-naphthalene-2-carbonitrile; NMR (CDCl$_3$) 8.05 (s,1), 7.85 (d,1), 7.8 (d,1), 7.55 (m,3), 7.45 (d,1), 7.4 (s,1), 7.2 (m,8), 7.0 (m,4), 5.1 (s,2), 5.0 (s,2) ppm; and 3,4-[[2,3-dihydro-4,5-diphenyl-2-oxo-1H-imidazol-1,3-diyl]bis(methylene)]-bis(benzonitrile).

PREPARATION 7

3-[(3-(3-methoxycarbonylphenyl)methyl-2,3-dihydro-4,5-diphenyl-2-oxo-1H-imidazol-1-yl) methyl]benzonitrile A. In a manner similar to Preparation 2 above, a suspension of 2-(3-methoxycarbonylphenyl)methyl-dihydro-4,5-diphenyl-1H-imidazol-2-one (410 mg, 1.1 mmol) (as prepared above in Preparation 5), cesium carbonate (1.5 g) and 4-methoxy-3-bromomethylbenzonitrile (0.2 g, 1 mmol) in 2 mL DMF was stirred at ambient temperature for 3 hours. The mixture was poured into 50 mL water and extracted with ethyl acetate (3×50 mL). The ethyl acetate layer was washed with water, dried and evaporated to afford 0.55 g of 4-methoxy-3-[(3-(3-methoxycarbonylphenyl)methyl-2,3-dihydro-4,5-diphenyl-2-oxo-1H-imidazol-1-yl)methyl] benzonitrile as a white solid.

B. To the ester formed above (0.5 g) in 5 mL MeOH was added 5 mL of 25% NaOH and the reaction stirred at ambient temperatures for 30 minutes. The reaction was acidified to pH 4 with 1N HCl and extracted with ethyl acetate (3×50 mL). The ethyl acetate layer was dried and evaporated to afford 0.4 g of the acid, 4-methoxy-3-[(3-(3-carboxyphenyl)methyl-2,3-dihydro-4,5-diphenyl-2-oxo-1H-imidazol-1-yl)methyl]benzonitrile as a white solid.

PREPARATION 8

3-[(3-(3-dimethylaminocarbonylphenyl)methyl-2,3-dihydro-4,5-diphenyl-2-oxo-1H-imidazol-1-yl) methyl]benzonitrile A. To a solution of 4-methoxy-3-[(3(3-carboxyphenyl) methyl-2,3-dihydro-4,5-diphenyl-2-oxo-1H-imidazol-1-yl) methyl]benzonitrile (0.39 g, 0.72 mmol), as prepared above in Preparation 7, in 5 mL DMF was added N,N-carbonyldiimidazole (166 mg, 1 mmol) and the reaction stirred at ambient temperatures for 2 hours. Dimethylamine (0.5 mL of 2M solution in THF) was added and the reaction stirred 10 h at ambient temperatures. The reaction mixture was poured into 50 mL 1N HCl and extracted with EtOAc. The organic layer was washed with water, dried and evaporated to afford 0.17 g of 4-methoxy-3-[(3-(3-dimethylaminocarbonylphenyl)methyl-2,3-dihydro-4,5-diphenyl-2-oxo-1H-imidazol-1-yl)methyl]benzonitrile as a white solid.

EXAMPLE 1

4,4'-[(2-Oxoimidazolin-1,3-diyl)bis(methylene)]bis (benzamidine), Dihydrochloride A. To 4,4'-[(2-oxoimidazolin-1,3-diyl)bis(methylene]bis (benzonitrile) (5 g, 16 mmol) in ethanol (20 mL) and methylene chloride (20 mL) at 0° C. was bubbled hydrochloric acid (g). After sealing the reaction vessel and stirring in a high-pressure flask for 16 hours, the reaction mixture was poured into ether to obtain a solid. The solid was collected by filtration and washed with ether. To the solid was added ethanol (40 mL) and the mixture was cooled to 0° C. Ammonia was bubbled into the reaction mixture. After sealing the reaction vessel, and heating at 55° C. for 4 hours, the mixture was cooled, poured into ether and the solid was collected by filtration. Recrystallization from ethanol gave 4,4'-[(2-oxoimidazolin-1,3-diyl)bis(methylene)]bis (benzamidine), dihydrochloride. Further purification by high performance liquid chromatography (HPLC) was sometimes necessary to give the final product. In such instances, the dihydrochloride salt was often replaced by trifluoroacetic acid (TFA) salt; NMR (DMSO-d$_6$) 9.3 (s,4), 9.0 (s,4), 7.8 (d,4), 7.5 (d,4), 4.45 (s,4), 3.25 (s,4) ppm.

B. In a similar manner, the following compounds were made:

3,3'-[(1,2-dihydro-2-oxo-1H-benzimidazol-1,3-diyl)bis (methylene)]bis(benzamidine), dihyclrochloride; NMR (DMSO-d$_6$) 9.35 (s,4), 9.0 (s,4), 7.8 (s,2), 7.7 (m,4), 7.55 (t,2), 7.1 (m,2), 7.0 (m,2), 5.2 (s,4) ppm;

4,4'-[(1,2-dihydro-4-methyl-2-oxo-1H-benzimidazol-1,3-diyl)bis(methylene)]-bis(benzamidine), dihydrochloride; NMR (DMSO-d$_6$) 9.3 (s,4), 9.0 (s,4), 7.8 (d,4), 7.55 (d,2), 7.35 (d,2), 7.0 (d,1), 6.9 (t,1), 6.75 (t,1), 5.43 (s,2), 5.22 (s,2), 2.25 (s,3) ppm;

4,4'-[(1,2,3,4,5,6-hexahydro-2-oxopyrimidin-1,3-diyl)bis (methylene)]bis(benzamidine), dihydrochloride; NMR (DMSO-d$_6$) 9.3 (s,4), 9.0 (s,4), 7.8 (d,4), 7.5 (d,2), 4.6 (s,4), 3.25 (m,4), 1.9 (m,2) ppm;

4,4'-[(1,2-dihydro-4,7-dimethyl-2-oxo-1H-benzimidazol-1, 3-diyl)bis(methylene)]-bis(benzamidine), dihydrochloride; NMR (DMSO-d$_6$) 9.35 (s,4), 9.05 (s,4), 7.82 (d,4), 7.4 (d,2), 6.7 (s,2), 5.5 (s,4), 2.25 (s,6) ppm;

3,3'-[(1,2-dihydro-4-methyl-2-oxo-1H-benzimidazol-1,3-diyl)bis(methylene)]-bis(benzamidine), dihydrochloride; NMR (DMSO-d$_6$) 9.3 (br,8), 7.6–7.9 (m,6), 7.45 (d,2), 7.05 (d,1), 6.95 (t,1), 6.8 (t,1), 5.43 (s,2), 5.25 (s,2), 2.3 (s,3) ppm;

3,3'-[(1,2-dihydro-4,7-dimethyl-2-oxo-1H-benzimidazol-1, 3-diyl)bis(methylene)]-bis(benzamidine), dihydrochloride; NMR (DMSO-$_6$) 9.35 (s,4), 8.95 (s,4), 7.2– 7.8 (m,8), 6.65 (s,2), 5.45 (s,2), 5.4 (s,2), 2.25 (s,3) ppm;

3,3'-[(5,6-dichloro-1,2-dihydro-2-oxo-1H-benzimidazol-1, 3-diyl)bis(methylene)]-bis(benzamidine), dihydrochloride; NMR (DMSO-d$_6$) 9.38 (s,4), 9.05 (s,4), 7.8 (s,2), 7.72 (m,4), 7.6 (t,2), 7.5 (s,2), 5.2 (s,4) ppm;

1,3-bis[3-(amidino)benzyl]-1,2-dihydro-5-ethyl-2oxo-1H-imidazole-4-carboxylic acid methyl ester, dihydrochloride; NMR (DMSO-d$_6$) 9.4 (s,4), 9.15 (s,2), 9.05 (s,2), 7.73 (m,4), 7.58 (m,4), 5.25 (s,2) 5.1 (s,2), 3.7 (s,3), 2.75 (q,2), 0.97 (t,3) ppm;

3,3'-[(4,5-diethyl-2,3-dihydro-2-oxo-1H-imidazol-1,3-diyl) bis(methylene)]-bis(benzamidine), dihydrochloride; NMR (DMSO-d$_6$) 9.4 (s,4), 9.1 (s,4), 7.7 (m,4), 7.58 (t,2), 7.44 (d,2), 4.95 (s,4), 2.35 (q,4), 0.9 (t,6) ppm;

1,3-bis[3-(amidino)benzyl]-1,2-dihydro-2-oxo-1H-imidazole-4,5-dicarboxylicacid, diethyl ester, dihydrochloride; NMR (DMSO-d$_6$) 9.35 (s,4), 9.05 (s,4), 7.7 (m,4), 7.58 (m,4), 5.2 (m,4), 4.18 (q,4), 1.15 (t,6) ppm;

4,4'-[(2,3-dihydro-4,5-diphenyl-2-oxo-1H-imidazol-1,3-diyl)bis(methylene)]-bis(benzamidine), trifluoroacetic acid salt; NMR (DMSO-d$_6$) 9.3 (s,4), 9.1 (s,4), 7.78 (d,4), 7.25 (m,10), 7.2 (m,4), 4.98 (s,4) ppm;

3,3'-[(2,3-dihydro-2-oxo-4-phenyl-1H-imidazol-1,3-diyl)
bis(methylene)]bis(benzamidine), trifluoroacetic acid
salt; NMR (DMSO-d$_6$) 9.35 (s,2), 9.3 (s,2), 9.05 (s,2), 9.0
(s,2), 7.4–7.8 (m,9), 7.3 (m,9), 6.88 (s,1), 5.03 (s,2), 4.97
(s,2) ppm;

3,3'-[(2,3-dihydro-4-methyl-2-oxo-5-phenyl-1H-imidazol-
1,3-diyl)bis(methylene)]-bis(benzamidine), trifluoroace-
tic acid salt; NMR (DMSO-d$_6$) 9.38 (s,2), 9.3 (s,2), 9.05
(s,2), 9.0 (s,2), 7.2–7.8 (m,13), 5.01 (s,2), 4.9 (s,2), 2.0
(s,3) ppm;

3,3'-[[2,3-dihydro-4-(4-dimethylaminophenyl)-2-oxo-5-
phenyl-1H-imidazol-1,3-diyl]bis(methylene)]bis
(benzamidine), trifluoroacetic acid salt; NMR (DMSO-
d$_6$) 9.3 (s,4), 9.03 (s,2), 9.0 (s,2), 7.65 (m,2), 7.5 (m,4),
7.25 (m,11), 4.95 (s,4), 3.03 (s,6) ppm;

3,3'-[(2,3-dihydro-4,5-bis(4-methoxyphenyl)-2-oxo-1H-
imidazol-1,3-diyl]bis(methylene)]-bis(benzamidine), trif-
luoroacetic acid salt; NMR (DMSO-d$_6$) 9.3 (s,4), 9.03
(s,4), 7.65 (d,2), 7.52 (m,4), 7.32 (d,2), 7.08 (d,4), 6.9
(d,4), 4.9 (s,4), 3.7 (s,6) ppm;

7-[[3-[3-(amidino)benzyl]-2,3-dihydro-4,5-diphenyl-2-oxo-
1H-imidazol-1,3-yl]methyl]-naphthalene-2-
carboximidamide, trifluoroacetic acid salt; NMR
(DMSO-d$_6$) 9.45 (s,2), 9.35 (s,2), 9.15 (s,2), 9.05 (s,2),
8.4 (s,1), 8.1 (d,1), 7.98 (d,1), 7.8 (d,1), 7.66 (m,2), 7.55
(m,2), 7.45 (d,1), 7.35 (d,1), 7.2 (m,10), 5.05 (s,2), 5.0
(s,2) ppm;

7-[[3-[4-(amidino)benzyl]-2,3-dihydro-4,5-diphenyl-2-
oxo-1H-imidazol-1-yl]methyl]-naphthalene-2-
carboximidamide, trifluoroacetic acid salt; NMR
(DMSO-d$_6$) 9.4 (s,2), 9.25 (s,2), 9.1 (s,2), 9.0 (s,2), 8.4
(s,1), 8.05 (d,1), 7.98 (d,1), 7.75 (m,3), 7.65 (s,1), 7.4
(d,1), 7.2 (m,12), 5.05 (s,2), 5.0 (s,2) ppm;

7,7'-[[2,3-dihydro-4,5-diphenyl-2-oxo-1H-imidazol-1,3-
diyl]bis(methylene)]-bis(naphthalene-2-
carboximidamide), trifluoroacetic acid salt; NMR
(DMSO-d$_6$) 9.4 (s,4), 9.1 (s,4), 8.4 (s,2), 8.1 (d,2), 8.0
(d,2), 7.8 (d,2), 7.68 (s,2), 7.45 (d,2), 7.2 (m,10), 5.1 (s,4)
ppm;

3,3'-[[2,3-dihydro-4-ethyl-2-oxo-5-phenyl-1H-imidazol-1,
3-diyl]bis(methylene)]-bis(benzamidine), trifluoroacetic
acid salt; NMR (DMSO-d$_6$) 9.36 (s,2), 9.3 (s,2), 9.05
(s,2), 9.0 (s,2), 7.78 (s,1), 7.75 (d,1), 7.4–7.7 (m,5), 7.37
(m,3), 7.23 (m,3), 5.02 (s,2), 4.85 (s,2), 2.35 (q,2), 0.92
(t,3) ppm;

3,3'-[[4,5-bis(methylethyl)-2,3-dihydro-2-oxo-1H-
imidazol-1,3-diyl]bis(methylene)]-bis(benzamidine), trif-
luoroacetic acid salt; NMR (DMSO-d$_6$) 9.38 (s,4), 9.07
(s,4), 7.7 (m,4), 7.6 (t,2), 7.3 (m,2), 5.02 (s,2), 5.03 (s,4),
3.0 (m,2), 1.1 (d,12) ppm;

3,4-[[2,3-dihydro-4,5-diphenyl-2-oxo-1H-imidazol-1,3-
diyl]bis(methylene)]-bis(benzamidine), trifluoroacetic
acid salt; NMR (DMSO-d$_6$) 9.3 (s,2), 9.28 (s,2), 9.0 (s,4),
7.73 (d,2), 7.66 (d,1), 7.5 (m,2), 7.25 (m,9), 7.18 (m,4),
4.98 (s,2), 4.95 (s,2) ppm;

3,3'-[(1,2-dihydro-2-oxo -4,5,6,7-tetrachloro-1H-
benzimidazol-1,3-diyl)bis(methylene)]-bis
(benzamidine), dihydrochloride; NMR (DMSO-d$_6$) 9.38
(s,4), 9.1 (s,4), 7.7 (m,4), 7.6 (m,4), 5.58 (s,4) ppm;

4,4'-[(1,2-dihydro-2-oxo-4,5,6,7-tetrachloro-1H-
benzimidazol-1,3-diyl)bis(methylene)]-bis
(benzamidine), dihydrochloride; NMR (DMSO-d$_6$) 9.20
(s,4), 8.80 (s,4), 7.80 (d,4), 7.40 (d,4), 5.60 (d,4) ppm;

3-[(3-((3-aminocarbonyl)phenyl)methyl-2,3-dihydro-4-
ethyl-2-oxo-5-phenyl-1H-imidazol-1-yl)methyl)
benzamidine, trifluoroacetic acid salt;

3-[(3-((3-aminocarbonyl)phenyl)methyl-2,3-dihydro-5-
ethyl-2-oxo-4-phenyl-1H-imidazol-1-yl)methyl)
benzamidine, trifluoroacetic acid salt;

3-[(3-((3-aminocarbonyl)phenyl)methyl-2,3-dihydro-4,5-
bis(4-methoxyphenyl)-2-oxo-1H-imidazol-1-yl)methyl)
benzamidine, trifluoroacetic acid salt;

3-[(3-(3-amidino-6-hydroxy)benzyl-2,3-dihydro-4,5-
diphenyl-2-oxo-1H-imidazol-1-yl)-methyl]benzamidine,
trifluoroacetic acid salt; NMR (DMSO-d$_6$) 9.20 (s,2), 9.15
(s,2), 9.00 (s,2), 8.70 (s,2), 6.90–7.60 (m,17), 4.80 (s,2),
5.00 (s,2) ppm;

3-[(3-(3-amidino-6-methoxy)benzyl-2,3 -dihydro-4,5-
diphenyl-2-oxo-1H-imidazol-1-yl)-methyl]benzamidine,
trifluoroacetic acid salt; NMR (DMSO-d$_6$) 9.30 (s,2), 9.20
(s,2), 8.90 (s,2), 8.80 (s,2), 7.00–7.70 (m,17), 5.00 (s,2),
4.90 (s,2), 3.70 (s,3) ppm;

4,4'-bis(methoxy)-3,3'-[(2,3- dihydro-4,5-diphenyl-2-oxo-
1H-imidazol-1,3-diyl)-bis(methylene)]bis(benzamidine),
trifluoroacetic acid salt; NMR (DMSO-d$_6$) 9.20 (s,4), 8.80
(s,4), 7.10–7.70 (m,16), 4.80 (s,4), 3.70 (s,3) ppm;

4,4'-bis (hydroxy)-3,3'-[(2,3-dihydro-4,5-diphenyl-2-oxo-
1H-imidazol-1,3-diyl)-bis(methylene)]bis(benzamidine),
trifluoroacetic acid salt; NMR (DMSO-d$_6$) 10.90 (s,2),
9.10 (s,4), 8.80 (s,4), 6.90–7.60 (m,16), 4.80 (s,4) ppm;

3,3'-[(2,3-dihydro-4,5-dimethyl-2-oxo-1H-imidazol-1,3-
diyl)bis(methylene)]-bis(benzamidine); NMR (DMSO-
d$_6$) 9.40 (s,4), (9.20 (s,4), 7.40–7.80 (m,8), 4.90 (s,4), 1.90
(s,6) ppm;

3,3'-[(4,4,7,7-tetramethyl-2-oxo-1,3-diazahepta-1,3-diyl)bis
(methylene)]-bis(benzamidine); m.p. 247°–249° C.;

3,3'-[(2-oxo-1,3-diazahepta-1,3-diyl)bis(methylene)]bis
(benzamidine); NMR (DMSO-d$_6$) 9.40 (br,8), 7.40–7.80
(m,8), 4.50 (s,4), 3.20 (br,4), 1.60 Co,4) ppm; m.p.
109°–111° C.;

4,4'-[(2-oxo-1,3-diazapenta-1,3-diyl)bis(methylene)]bis
(benzamidine); NMR (DMSO-d$_6$) 9.30 (s,4), 9.20 (s,4),
7.80 (d,4), 7.60 (d,4), 4.30 (s,4), 3.20 (br,4), 1.60 for,4)
ppm; and 4-methoxy-3-[3-(3-dimethylaminocarbonylphenyl)methyl-
2,3-dihydro-4,5-diphenyl-2-oxo-1H-imidazol-1-yl)
methyl]benzonitrile; NMR (DMSO-d$_6$) 9.25 (s ,4), 8.80
(s,4), 7.00–7.70 (m,17), 4.80 (s,2), 4.82 (s,2), 3.70 (s,6).

EXAMPLE 2

4,4'-[(1,2-Dihydro-2-oxo-1H-benzimidazol-1,3-diyl)
bis(methylene)]bis(benzamidine), Methanesulfonic
Acid Salt A. In a manner similar to Example 1 above, 4,4'-[(1,2-
dihydro-2-oxo-1H-benzimidazol-1,3-diyl)bis(methylene)]
bis(benzonitrile) (1.6 g, 4.4 mmol) was reacted sequentially
with hydrochloric acid and ethanolic ammonia. The result-
ing solid was dissolved in water and free-based with sodium
hydroxide (aq). The solid was collected by filtration and
dissolved in methanol. Methanesulfonic acid was added to
the solution (1:1 equivalent/amidine), followed by ether
until crystallization. The crystals were collected by filtration
and dried to give 4,4'-[(1,2-dihydro-2-oxo-1H-
benzimidazol-1,3-diyl)bis(methylene)]bis(benzamidine),
methanesulfonic acid salt; NMR (DMSO-d$_6$) 9.3 (s,4), 9.0
(s,4), 7.8 (d,4), 7.55 (d,4), 7.1 (m,2), 7.0 (m,2); 5.22 (s,4),
2.5 (s,6) ppm.

B. In a similar manner, the following compounds were
made:

3,3'-[(2-oxoimidazolin-1,3-diyl)bis(methylene)]bis
(benzamidine), dihydrochloride; NMR (DMSO-d$_6$) 9.35
(s,4), 9.05 (s,4), 7.7 (m,4), 7.6 (d,4), 4.42 (s,4), 3.25 (s,4),
2.5 (s,6) ppm;

3,3'-[(2-oxo-4,4,5,5-tetramethylimidazolin-1,3-diyl)bis
(methylene)]bis(benzamidine), methanesulfonic acid salt;

NMR (DMSO-d$_6$) 9.25 (s,4), 8.9 (s,4), 7.73 (s,2), 7.65 (m,4), 7.5 (t,2), 4.35 (s,4), 2.55 (s,6), 1.0 (s,12) ppm;

4,4'-[(2-oxo-4,4,5,5-tetramethylimidazolin-1,3-diyl)bis(methylene)]bis(benzamidine), methanesulfonic acid salt; and 3,3'-[(2,3-dihydro-4,5-diphenyl-2-oxo-1H-imidazol-1,3-diyl)bis(methylene)]-bis(benzamidine), methanesulfonic acid salt; NMR (DMSO-d$_6$) 9.25 (s,4), 8.98 (s,4), 7.65 (d,2), 7.5 (m,4), 7.1–7.3 (m,12), 4.95 (s,4), 2.5 (s,6) ppm.

EXAMPLE 3

3,3'-[(2,3-Dihydro-4-ethyl-2-oxo-1H-imidazol-1,3-diyl)bis(methylene)]bis(benzamidine), Trifluoroacetic Acid Salt To 50% aqueous sodium hydroxide was added 1,3-bis[3-(amidino)benzyl]-1,2-dihydro-5-ethyl-2-oxo-1H-imidazole-4-carboxylic acid, methyl ester, dihydrochloride (0.20 g, 0.46 mmol). After stirring for 30 minutes, carbon dioxide (g) was bubbled through the solution to neutralize excess hydrochloride and methanol (1 mL) was added. The solid was removed by filtration and the flitrate was concentrated in vacuo. After adjusting the pH to 6 with 3N hydrochloric acid (aq), the material was purified by high performance liquid chromatography (HPLC) to give 3,3'-[(2,3-dihydro-4-ethyl-2-oxo-1H-imidazol-1,3-diyl)bis(methylene)]bis(benzamidine), trifluoroacetic acid salt; NMR (DMSO-d$_6$) 9.4 (s,4), 9.35 (s,4), 7.65 (d,2), 7.4–7.9 (m,8), 6.35 (s,1), 4.95 (s,2), 4.9 (s,2), 2.3 (q,2), 1.05 (t,3) ppm.

EXAMPLE 4

1,3-Bis[3-(amidino)benzyl]-1,2-dihydro-2-oxo-1H-imidazole-4,5-dicarboxylic Acid, Dihydrochloride To 1,3-bis[3-(amidino)benzyl]-1,2-dihydro-2-oxo-1H-imidazole-4,5-dicarboxylic acid, diethyl ester, dihydrochloride (0.1 g, 0.20 mmol) in methanol (1 mL)/water (1 mL) at 0° C. was added 50% aqueous sodium hydroxide (2 mL). After stirring for 2 hours, the pH was adjusted to 1 with 3N hydrochloric acid (aq). The resulting material was filtered and dried under vacuum to give 1,3-bis[3-(amidino)-benzyl]-1,2-dihydro-2-oxo-1H-imidazole-4,5-dicarboxylic acid, dihydrochloride; NMR (DMSO-d$_6$) 9.35 (s,4), 9.0 (s,4), 7.7 (m,4), 7.58 (m,4), 5.35 (s,4) ppm.

EXAMPLE 5

This example illustrates the preparation of representative pharmaceutical compositions for oral administration containing a compound of the invention, or a pharmaceutically acceptable salt thereof, e.g. , 3,3'-[(1,2-dihydro-2-oxo-4,5,6,7-tetrachloro-1H-benzimidazol-1,3-diyl)bis(methylene)]bis(benzamidine):

| A. Ingredients | % wt./wt. |
| --- | --- |
| Compound of the invention | 20.0% |
| Lactose | 79.5% |
| Magnesium stearate | 0.5% |

The above ingredients are mixed and dispensed into hard-shell gelatin capsules containing 100 mg each, one capsule would approximate a total daily dosage.

| B. Ingredients | % wt./wt. |
| --- | --- |
| Compound of the invention | 20.0% |
| Magnesium stearate | 0.9% |
| Starch | 8.6% |
| Lactose | 79.6% |
| PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| C. Ingredients | |
| --- | --- |
| Compound of the invention | 0.1 g |
| Propylene glycol | 20.0 g |
| Polyethylene glycol 400 | 20.0 g |
| Polysorbate 80 | 1.0 g |
| Water | q.s. 100 mL |

The compound of the invention is dissolved in propylene glycol, polyethylene glycol 400 and polysorbate 80. A sufficient quantity of water is then added with stirring to provide 100 mL of the solution which is ffitered and bottled.

| D. Ingredients | % wt./wt. |
| --- | --- |
| Compound of the invention | 20.0% |
| Peanut Oil | 78.0% |
| Span 60 | 2.0% |

The above ingredients are melted, mixed and filled into soft elastic capsules.

| E. Ingredients | % wt/wt |
| --- | --- |
| Compound of the invention | 1.0% |
| Methyl or carboxymethyl cellulose | 2.0% |
| 0.9% saline | q.s. 100 mL |

The compound of the invention is dissolved in the cellulose/saline solution, filtered and bottled for use.

EXAMPLE 6

This example illustrates the preparation of a representative pharmaceutical formulation for parenteral administration containing a compound of the invention, or a pharmaceutically acceptable salt thereof, e.g., 3,3'-[(2,3-dihydro-4,5-diphenyl-2-oxo-1H-imidazol-1,3-diyl)bis(methylene)]bis(benzamidine):

| Ingredients | |
| --- | --- |
| Compound of the invention | 0.02 g |
| Propylene glycol | 20.0 g |
| Polyethylene glycol 400 | 20.0 g |
| Polysorbate 80 | 1.0 g |
| 0.9% Saline soiution | q.s. 100 mL |

The compound of the invention is dissolved in propylene glycol, polyethylene glycol 400 and polysorbate 80. A sufficient quantity of 0.9% saline solution is then added with stirring to provide 100 mL of the I.V. solution which is filtered through a 0.2µ membrane filter and packaged under sterile conditions.

EXAMPLE 7

This example illustrates the preparation of a representative pharmaceutical composition in suppository form containing a compound of the invention, or a pharmaceutically acceptable salt thereof, e.g., 3,3'-[[2,3-dihydro-4-(4-dimethylaminophenyl-2-oxo-5-phenyl-1H-imidazol-1,3-diyl]bis(methylene)]bis(benzamidine):

| Ingredients | % wt./wt. |
|---|---|
| Compound of the invention | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 8

This example illustrates the preparation of a representative pharmaceutical formulation for insufflation containing a compound of the invention, or a pharmaceutically acceptable salt thereof, e.g., 7-[[3-[4-(amidino)benzyl]-2,3-dihydro-4,5-diphenyl-2-oxo-1H-imidazol-1-yl]methyl]-naphthalene-2-carboximidamide:

| Ingredients | % wt./wt. |
|---|---|
| Micronized compound of the invention | 1.0% |
| Micronized lactose | 99.0% |

The ingredients are milled, mixed, and packaged in an insufflator equipped with a dosing pump.

EXAMPLE 9

This example illustrates the preparation of a representative pharmaceutical formulation in nebulized form containing a compound of the invention, or a pharmaceutically acceptable salt thereof, e.g., 7-[[3-[3-(amidino)benzyl]-2,3-dihydro-4,5-diphenyl-2-oxo-1H-imidazol-1-yl]methyl] naphthalene-2-carboximidamide:

| Ingredients | % wt./wt. |
|---|---|
| Compound of the invention | 0.005% |
| Water | 89.995% |
| Ethanol | 10.000% |

The compound of the invention is dissolved in ethanol and blended with water. The formulation is then packaged in a nebulizer equipped with a dosing pump.

EXAMPLE 10

This example illustrates the preparation of a representative pharmaceutical formulation in aerosol form containing a compound of the invention, or a pharmaceutically acceptable salt thereof, e.g., 7,7'-[[2,3-dihydro-4,5-diphenyl-2-oxo-1H-imidazol-1,3-diyl]bis(methylene)]bis(naphthalene-2-carboximidamide):

| Ingredients | % wt./wt. |
|---|---|
| Compound of the invention | 0.10% |
| Propellant 11/12 | 98.90% |
| Oleic acid | 1.00% |

The compound of the invention is dispersed in oleic acid and the propellants. The resulting mixture is then poured into an aerosol container fired with a metering valve.

EXAMPLE 11

(In vitro assay for Factor Xa and Thrombin)

This assay demonstrates the activity of the compounds of the invention towards factor Xa, thrombin and tissue plasminogen activator. The activities were determined as an initial rate of cleavage of the peptide p-nitroanilide by the enzyme. The cleavage product, p-nitroaniline, absorbs at 405 nm with a molar extinction coefficient of 9920 $M^{-1}cm^{-1}$.

Reagents and Solutions:
Dimethyl sulfoxide (DMSO) (Baker analyzed grade).
Assay buffer: 50 mM TrisHCl, 150 mM NaCl, 2.5 mM $CaCl_2$, and 0.1% polyethylene glycol 6000, pH 7.5.
Enzymes (Enzyme Research Lab.):

1. Human factor Xa stock solution: 0.281 mg/mL in assay buffer, stored at –80° C. (working solution (2×): 106 ng/mL or 2 nM in assay buffer, prepared prior to use).

2. Human thrombin stock solution: Stored at –80° C. (working solution (2×): 1200 ng/mL or 40 nM in assay buffer, prepare prior to use).

3. Humam tissue plasminogen activator (tPA) (Two chains, Sigma) stock solution: 1 mg/mL, stored at –80° C. (working solution (2×): 1361 ng/mL in assay buffer, prepare prior to use).

Chromogenie substrates (Pharmacia Hepar Inc.):

1. S2222 (FXa assay) stock solution: 6 mM in $dH_2O$, store at 4° C. (working solution (4×): 656 µM in assay buffer).

2. S2302 (Thrombin assay) stock solution: 10 mM in $dH_2O$, stored at 4° C. (working solution (4×): 1200 µM in assay buffer).

3. S2288 (tPA assay) stock solution: 10 mM in $dH_2O$, stored at 4° C. (working solution (4×): 1484 µM in assay buffer).

(All substrate working solutions were prepared on assay day 5.)

Standard inhibitor compound stock solution: 5 mM in DMSO, stored at –20° C.

Test compounds (compounds of the invention) stock solutions: 10 mM in DMSO, stored at –20° C.

Assay Procedure:

Assays were performed in 96-well microtiter plates in a total volume of 200 µl. Assay conducted in final concentration of 50 mM TrisHCl, 150 mM NaCl, 2.5 mM $CaCl_2$, 0.1% polyethylene glycol 6000, pH 7.5, in the absence or presence of the standard inhibitor or the test compounds and enzyme and substrate at following concentrations: (1) 1 nM factor Xa and 164 µM S2222; (2) 20 nM thrombin and 300 µM S2302; and (3) 10 nM tPA and 371 µM S2288. Concentrations of the standard inhibitor compound in the assay were from 5 µM to 0.021 µM in 1 to 3 dilution. Concentration of the test compounds in the assay typically were from 10 µM to 0.041 nM in 1 to 3 dilution. For potent test compounds, the concentrations used in the factor Xa assay were further diluted 100 fold (100 nM to 0.41 nM) or 1000 fold (10 nM to 0.041 nM). All substrate concentrations used are equal to their $K_m$ values under the present assay conditions. Assays were performed at ambient temperature.

The first step in the assay was the preparation of 10 mM test compound stock solutions in DMSO (for potent test compounds, 10 mM stock solutions were further diluted to 0.1 or 0.01 mM for the factor Xa assay), followed by the preparation of test compound working solutions (4×) by a serial dilutions of 10 mM stock solutions with Biomek 1000 (or Multiprobe 204) in 96 deep well plates as follows:

(a) Prepare a 40 µM working solution by diluting the 10 mM stock 1 to 250 in assay buffer in 2 steps: 1 to 100, and 1 to 2.5.

(b) Make another five serial dilutions (1:3) of the 40 µM solution (600 µl for each concentration). A total of six diluted test compound solutions were used in the assay. Standard inhibitor compound (5 mM stock) or DMSO (control) went through the same dilution steps as those described above for test compounds.

The next step in the assay was to dispense 50 µl of the test compound working solutions (4×) (from 40 uM to 0.164 uM), in duplicate, to microtiter plates with Biomek or MP204. To this was added 100 µl of enzyme working solution (2×) with Biomek or MP204. The resulting solutions were incubated at ambient temperature for 10 minutes.

To the solutions was added 50 µl of substrate working solution (4×) with Biomek or MP204.

The enzyme kinetics were measured at 405 nm, at 10 seconds interval, for five minutes in a THERMOmax plate reader at ambient temperature.

Calculation of $K_i$ of the BX compounds:

Enzyme rates were calculated as mOD/min based on the first two minutes readings. The $IC_{50}$ values were determined by fitting the data to the log-logit equation (linear) or the Morrison equation (non-linear) with an EXCEL spreadsheet. Ki values were then obtained by dividing the $IC_{50}$ by 2. Routinely, Ki(factor Xa) values lower than 3 nM were calculated from the Morrison equation.

Compounds of the invention, when tested in this assay, demonstrated the ability to inhibit human factor Xa and human thrombin.

EXAMPLE 12

(In vitro assay for Human Prothrombinase)

This assay demonstrates the ability of the compounds of the invention to inhibit prothrombinase. Prothrombinase (PTase) catalyzes the activation of prothrombin to yield fragment 1.2 plus thrombin with meizothrombin as the intermediate. This assay is an end point assay. Activity of the prothrombinase is measured by activity of thrombin (one of the reaction products) or by the mount of thrombin formed/time based on a thrombin standard curve (nM vs mOD/min). For determination of $IC_{50}$ (PTase) of the compounds of the invention, PTase activity was expressed by thrombin activity (mOD/min).

Materials:
Enzymes:

1. Human factor Va (Haematologic Technologies Inc., Cat# HCVA-0110) working solution: 1.0 mg/mL in 50% glycerol, 2 mM $CaCl_2$, stored at −20° C.

2. Human factor Xa (Enzyme Res. Lab. cat# HFXa1011) working solution: 0.281 mg/mL in assay buffer (without BSA), stored at −80° C.

3. Human prothrombin (FII) (Enzyme Res. Lab., Cat#HP1002) working solution: Diluted FII to 4.85 mg/mL in assay buffer (without BSA), stored at −80° C.

Phospholipid (PCPS) vesicles:

PCPS vesicles (80%PC, 20%PS) were prepared by modification of the method reported by Barenholz et al., *Biochemistry* (1977), Vol. 16, pp. 2806–2810. Phosphatidyl serine (Avanti Polar Lipids, Inc., Cat# 840032): 10 mg/mL in chloroform, purified from brain, stored −20° C. under nitrogen or argon.

Phosphatidyl Choline (Avanti Polar Lipids, Inc., Cat# 850457): 50 mg/ml in chloroform, synthetic 16:0–18:1 Palmitoyl-Oleoyl, stored at −20° C. under nitrogen or argon.

Spectrozyme-TH (American Diagnostica Inc., Cat# 238L, 50 µmoles, stored at room temperature) working solution: Dissolved 50 µmoles in 10 mL $dH_2O$.

BSA (Sigma Chem Co., Cat#A-7888, FractionV, RIA grade).

Assay buffer: 50 mM TrisHCl, pH 7.5, 150 mM NaCl, 2.5 mM $CaCl_2$, 0.1% PEG 6000 (BDH), 0.05% BSA (Sigma, Fr.V, RIA grade).

For one plate assay, prepare the following working solutions:

1. Prothrombinase complex:
  (a) 100 µM PCPS (27.5 µl of PCPS stock (4.36 mM) diluted to final 1200 µl with assay buffer.
  (b) 25 nM Human factor Va: 5.08 µl of Va stock (1 mg/mL) was diluted to final 1200 µl with assay buffer.
  (c) 5 pM Human factor Xa: Dilute Xa stock (0.281 mg/mL) 1:1,220,000 with. assay buffer. Prepare at least 1200 µl.

Combine equal volumes (1100 µ) of each component in the order of PCPS, factor Va and factor Xa. Let stand at ambient temperature for 5 to 10 minutes and use immediately, or store in ice (bring to ambient temperature before use). 2. 6 µM Human prothrombin (FII): dilute 124 µL of FII stock (4.85 mg/mL) to final 1400 µL with assay buffer.

3. 20 mM EDTA/Assay buffer: 0.8 mL of 0.5M EDTA (pH 8.5) plus 19.2 mL assay buffer.

4. 0.2 mM Spectrozyme-TH/EDTA buffer: 0.44 mL of SPTH stock (5 mM) plus 10.56 mL of 20 mM EDTA/assay buffer.

5. Test compounds (compounds of the invention): Prepare a working solution (5×) from 10 mM stock (DMSO) and make a series of 1:3 dilution. Compounds were assayed at 6 concentrations in duplicate.

Assay conditions and procedure:

Prothrombinase reaction was performed in final 50 µL of mixture containing PTase (20 uM PCPS, 5 nM hFVa, and 1 pM hFXa), 1.2 uM human factor II and varied concentration of the test compounds (5 µM to 0.021 µM or lower concentration range). Reaction was started by addition of PTase and incubated for 6 minutes at room temperature. Reaction was stopped by addition of EDTA/buffer to final 10 mM. Activity of thrombin (product) was then measured in the presence of 0.1 mM of Spectrozyme-TH as substrate at 405 nm for 5 minutes (10 second intervals), at ambient temperature, in a THEROmax microplate reader. Reactions were performed in 96-well microtiter plates.

In the first step of the assay, 10 µl of diluted test compound (5×) or buffer was added to the plates in duplicate. Then 10 µl of prothombin (hFII) (5×) was added to each well. Next 30 µl PTase was added to each well, mix for about 30 seconds. The plates were then incubated at ambient temperature for 6 minutes.

In the next step, 50 µl of 20 mM EDTA (in assay buffer) was added to each well to stop the reaction. The resulting solutions were then mixed for about 10 seconds. Then 100 µl of 0.2 mM spectrozyme was added to each well. The

29 thrombin reaction rate was then measured at 405 nm for 5 minutes (at 10 second intervals) in a Molecular Devices microplate reader.

Calculations:

Thrombin reaction rate was expressed as mOD/minute using OD readings from the five minute reaction. $IC_{50}$ values were calculated with the log-logit curve fit program.

The compounds of the invention demonstrated the ability to inhibit thrombinase when tested in this assay.

EXAMPLE 13

(In vivo assay)

The following assay demonstrates the ability of the compounds to act as anti-coagulants.

Male rats (250–330 g) were anesthetized with sodium pentobarbital (90 mg/kg, i.p.) and prepared for surgery. The left carotid artery was cannulated for the measurement of blood pressure as well as for taking blood samples to monitor clotting variables (prothrombin time (PT) and activated partial thromboplastin time (aPTT)). The tail vein was cannulated for the purpose of administering the test compounds (i.e., the compounds of the invention and standards) and the thromboplastin infusion. The abdomen was opened via a mid-line incision and the abdominal vena cava was isolated for 2–3 cm distal to the renal vein. All venous branches in this 2–3 cm segment of the abdominal vena cava were ligated. Following all surgery the animals were allowed to stabilize prior to beginning the experiment. Test compounds were administered as an intravenous bolus (t=0). Three minutes later (t=3), a 5-minute infusion of thromboplastin was begun. Two minutes into the infusion (t=5), the abdominal vena cava was ligated at both the proximal and distal ends. The vessel was left in place for 60 minutes, after which it was excised from the animal, slit open, the clot (if any) carefully removed, and weighed. Statistical analysis on the results was performed using a Wilcoxin-matched-pairs signed rank test.

The compounds of the invention, when tested in this assay, demonstrated the ability to clot the blood.

While the present invention has been described with reference to the specific embodiments thereof, it should be understood by those skilled in the art that various changes may be made and equivalents may be substituted without departing from the true spirit and scope of the invention. In addition, many modifications may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

30

What is claimed is:

1. A compound of formula (II):

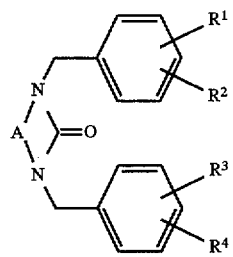

(II)

wherein:

A is —C($R^5$)($R^6$)—C($R^9$)($R^{10}$);

$R^1$ is —C(NH)$NH_2$, —C(NH)N(H)O$R^{11}$, —C(NH)N(H)C(O)$R^9$, or —C(NH)N(H)C(O)O$R^{11}$;

$R^2$ and $R^3$ are the same or different and are selected from the group consisting of independently hydrogen, halo, lower alkyl, lower haloalkyl, phenyl, naphthyl, —O$R^{11}$, —C(O)O$R^{11}$, —C(O)N($R^{11}$)$R^{12}$, —N($R^{11}$)$R^{12}$, —N(H)C(O)$R^{11}$, and —N(H)S(O)$_2R^{11}$;

$R^4$ is halo, lower haloalkyl, imidazolyl, —C(NH)$NH_2$, —C(NH)NHO$R^{11}$, —C(NH)N(H)C(O)$R^9$, —C(NH)N(H)C(O)O$R^{11}$, —O$R^{11}$, —C(O)$R^{13}$, —(CH$_2$)$_n$C(O)O$R^{11}$ (where n is 0 to 6), —C(O)N($R^{11}$)$R^{12}$, or —N($R^{11}$)$R^{12}$;

$R^5$, $R^6$, $R^9$ and $R^{10}$ are independently hydrogen, halo, lower alkyl, lower haloalkyl, 4-pyridinyl, —O$R^{11}$, —C(O)O$R^{11}$, —C(O)N($R^{11}$)$R^{12}$, phenyl (optionally substituted by one or more substituents selected from the group consisting of halo, hydroxy, lower alkyl, lower haloalkyl, lower alkoxy and —N($R^{11}$)$R^{12}$), or naphthyl (optionally substituted by one or more substituents selected from the group consisting of halo, hydroxy, lower alkyl, lower haloalkyl, lower alkoxy and —N($R^{11}$)$R^{12}$);

$R^{11}$ and $R^{12}$ are independently hydrogen, lower alkyl, phenyl, naphthyl or lower aralkyl; and $R^{13}$ is pyrrolidinyl, 4-morpholinyl, piperazinyl, N-methylpiperazinyl, or piperidinyl; or a pharmaceutically acceptable salt thereof.

2. A pharmaceutical composition useful in treating a human having a disease-state characterized by thrombotic activity, which composition comprises a therapeutically effective amount of a compound of formula (II):

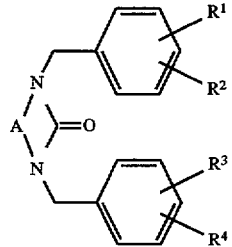

(II)

wherein:

A is —C($R^5$)($R^6$)—C($R^9$)($R^{10}$)—;

$R^1$ is —C(NH)$NH_2$, —C(NH)N(H)O$R^{11}$, —C(NH)N(H)C(O)$R^9$, or —C(NH)N(H)C(O)O$R^{11}$;

$R^2$ and $R^3$ are the same or different and are selected from the group consisting of independently hydrogen, halo, lower alkyl, lower haloalkyl, phenyl, naphthyl, —O$R^{11}$, —C(O)O$R^{11}$, —C(O)N($R^{11}$)$R^{12}$, —N($R^{11}$)$R^{12}$, —N(H)C(O)$R^{11}$, and —N(H)S(O)$_2R^{11}$;

$R^4$ is halo, lower haloalkyl, imidazolyl, —C(NH)NH$_2$, —C(NH)NHOR$^{11}$, —C(NH)N(H)C(O)R$^9$, —C(NH)N(H)C(O)OR$^{11}$, —OR$^{11}$, —C(O)R$^{13}$, —(CH$_2$)$_n$C(O)OR$^{11}$ (where n is 0 to 6), —C(O)N(R$^{11}$)R$^{12}$, or —N(R$^{11}$)R$^{12}$;

$R^5$, $R^6$, $R^9$ and $R^{10}$ are independently hydrogen, halo, lower alkyl, lower haloalkyl, 4-pyridinyl, —OR$^{11}$, —C(O)OR$^{11}$, —C(O)N(R$^{11}$)R$^{12}$, phenyl (optionally substituted by one or more substituents selected from the group consisting of halo, hydroxy, lower alkyl, lower haloalkyl, lower alkoxy and —N(R$^{11}$)R$^{12}$), or naphthyl (optionally substituted by one or more substituents selected from the group consisting of halo, hydroxy, lower alkyl, lower haloalkyl, lower alkoxy and —N(R$^{11}$)R$^{12}$);

$R^{11}$ and $R^{12}$ are independently hydrogen, lower alkyl, phenyl, naphthyl or lower aralkyl; and $R^{13}$ is pyrrolidinyl, 4-morpholinyl, piperazinyl, N-methylpiperazinyl, or piperidinyl; or a pharmaceutically acceptable salt thereof, and a pharmaceutically acceptable excipient.

\* \* \* \* \*